(12) United States Patent
Chen et al.

(10) Patent No.: US 10,379,061 B1
(45) Date of Patent: Aug. 13, 2019

(54) SYSTEMS, METHODS AND METRICS FOR WAFER HIGH ORDER SHAPE CHARACTERIZATION AND WAFER CLASSIFICATION USING WAFER DIMENSIONAL GEOMETRY TOOL

(71) Applicant: KLA-Tencor Corporation, Milpitas, CA (US)

(72) Inventors: Haiguang Chen, Mounatin View, CA (US); Jaydeep Sinha, Livermore, CA (US); Sergey Kamensky, Campbell, CA (US); Sathish Veeraraghavan, Santa Clara, CA (US); Pradeep Vukkadala, Newark, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/406,732

(22) Filed: Jan. 15, 2017

Related U.S. Application Data

(62) Division of application No. 13/656,143, filed on Oct. 19, 2012, now Pat. No. 9,546,862.

(51) Int. Cl.
  *G01N 21/95* (2006.01)
  *G01B 11/24* (2006.01)
  (Continued)

(52) U.S. Cl.
  CPC ......... *G01N 21/9501* (2013.01); *G01B 11/24* (2013.01); *G06K 9/6267* (2013.01);
  (Continued)

(58) Field of Classification Search
  None
  See application file for complete search history.

(56) References Cited

U.S. PATENT DOCUMENTS

| 5,083,378 A | 1/1992 | Juday |
| 5,521,036 A * | 5/1996 | Iwamoto ............... G03F 9/7026 250/548 |

(Continued)

FOREIGN PATENT DOCUMENTS

| JP | 2002188912 A | 7/2002 |
| JP | 2012083126 | 4/2012 |

OTHER PUBLICATIONS

U.S. Appl. No. 13/476,328, filed May 21, 2012, Vukkadala et al.
(Continued)

*Primary Examiner* — Tung S Lau
(74) *Attorney, Agent, or Firm* — Suiter Swantz pc llo

(57) ABSTRACT

Systems and methods for improving results of wafer higher order shape (HOS) characterization and wafer classification are disclosed. The systems and methods in accordance with the present disclosure are based on localized shapes. A wafer map is partitioned into a plurality of measurement sites to improve the completeness of wafer shape representation. Various site based HOS metric values may be calculated for wafer characterization and/or classification purposes, and may also be utilized as control input for a downstream application. In addition, polar grid partitioning schemes are provided. Such polar grid partitioning schemes may be utilized to partition a wafer surface into measurement sites having uniform site areas while providing good wafer edge region coverage.

14 Claims, 24 Drawing Sheets

(51) Int. Cl.
  *G06T 7/00* (2017.01)
  *G06T 7/60* (2017.01)
  *G06K 9/62* (2006.01)

(52) U.S. Cl.
  CPC .............. *G06T 7/0004* (2013.01); *G06T 7/60* (2013.01); *G06T 2207/20021* (2013.01); *G06T 2207/30148* (2013.01)

(56) References Cited

U.S. PATENT DOCUMENTS

| | | | | |
|---|---|---|---|---|
| 6,185,324 | B1* | 2/2001 | Ishihara | G01N 21/88 257/E21.525 |
| 7,038,773 | B2 | 5/2006 | Kuhlmann et al. | |
| 2004/0122624 | A1 | 6/2004 | Naruoka | |
| 2006/0004542 | A1* | 1/2006 | Koliopoulos | G01B 21/08 702/182 |
| 2006/0252246 | A1* | 11/2006 | Paik | H01L 27/14618 438/612 |
| 2007/0064224 | A1* | 3/2007 | Kreh | G01N 21/9501 356/237.2 |
| 2009/0136117 | A1* | 5/2009 | Barkol | G01N 21/93 382/145 |
| 2011/0144943 | A1 | 6/2011 | Veeraraghavan et al. | |
| 2012/0106827 | A1 | 5/2012 | Park et al. | |
| 2013/0089935 | A1 | 4/2013 | Vukkadala et al. | |
| 2013/0304399 | A1* | 11/2013 | Chen | G06T 7/0004 702/40 |

OTHER PUBLICATIONS

Vukkadala, Pradeep, et al., "Impact of Wafer Geometry on CMP for Advanced Nodes", Journal of the Electrochemical Society, 158(10) H1002-H1009, Aug. 3, 2011, 8 pages.
European Supplementary Search Report for Application No. 13846801.2, dated Mar. 31, 2016, 8 pages.

* cited by examiner

X Slope

Y Slope

Radial Slope

Tangential Slope

X Slope

Y Slope

Radial Slope

Tangential Slope

X Slope

Y Slope

Radial Slope

Tangential Slope

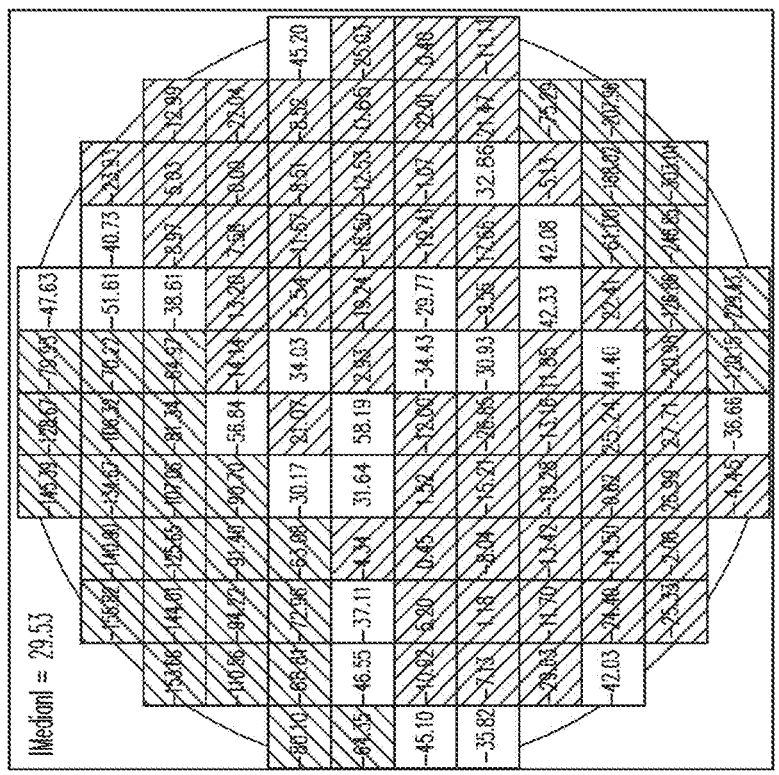
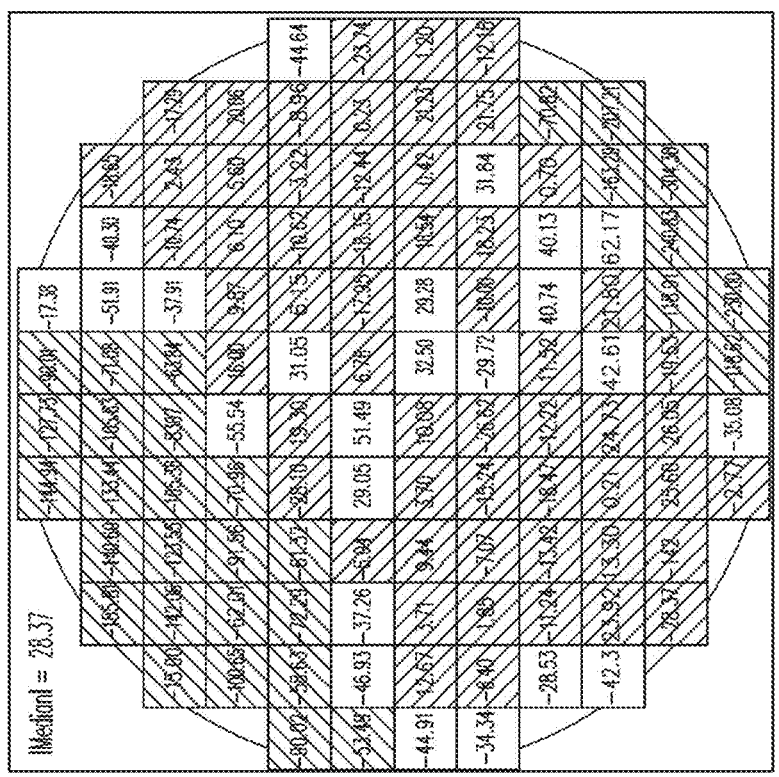
FIG. 15B
FIG. 15A

SYSTEMS, METHODS AND METRICS FOR WAFER HIGH ORDER SHAPE CHARACTERIZATION AND WAFER CLASSIFICATION USING WAFER DIMENSIONAL GEOMETRY TOOL

PRIORITY

The present application claims the benefit under 35 U.S.C. § 120(pre-AIA) of U.S. patent application Ser. No. 13/656,143, filed Oct. 19, 2012, issued as U.S. Pat. No. 9,546,862, which is incorporated herein by reference.

TECHNICAL FIELD

The disclosure generally relates to the field of wafer surface metrology, and particularly to systems and methods for wafer high order shape characterization and wafer classification.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Generally, certain requirements may be established for the flatness and thickness uniformity of the wafers. The semiconductor industry uses the two global wafer shape metrics, bow and warp, to describe the overall wafer shape. Global surface fitting using the Zernike polynomials or Taylor polynomials have also been used to describe the wafer shape components.

However, the two global wafer shape metrics, bow and warp, do not have the required spatial resolution and sensitivity for the local wafer shape characterization. Methods based on the whole wafer surface fitting cannot provide the information about the location of wafer local higher order shape components and often do not have good shape sensitivity even with very high polynomial fitting orders.

Therein lies a need for systems, methods and metrics for wafer high order shape characterization and wafer classification without the aforementioned shortcomings.

SUMMARY

The present disclosure is directed to a method for inspecting a wafer. The method may include: defining a wafer partitioning scheme; obtaining a wafer surface image; partitioning the wafer surface image into a plurality of measurement sites according to the wafer partitioning scheme; calculating a plurality of measurement metrics for each of the plurality of measurement sites based on the acquired wafer surface image; and reporting the plurality of measurement metrics calculated for each of the plurality of measurement sites in a graphical representation.

A further embodiment of the present disclosure is directed to a system for inspecting a wafer. The system may include an optical system configured for obtaining a wafer surface image. The system may also include a site based high order wafer shape analysis module in communication with the optical system. The site based high order wafer shape analysis module may be configured for: defining a wafer partitioning scheme; partitioning the wafer surface image into a plurality of measurement sites according to the wafer partitioning scheme; calculating a plurality of measurement metrics for each of the plurality of measurement sites based on the acquired wafer surface image; and reporting the plurality of measurement metrics calculated for each of the plurality of measurement sites in a graphical representation.

An additional embodiment of the present disclosure is directed to polar grid partitioning method for partitioning a wafer surface. The method may include: specifying a number of sectors and a number of zones required for the polar grid partitioning; calculating a sector angular span based on the number of sectors specified; calculating a radial span for each of the number of zones, wherein the radial span for a first zone having a first radial distance to the center of the wafer is different from the radial span for a second zone having a second radial distance to the center of the wafer; and partitioning the wafer surface into a plurality of sites based on the sector angular span and the radial span for each zone, wherein the plurality of sites have uniform site areas.

An additional embodiment of the present disclosure is directed to polar grid partitioning method for partitioning a wafer surface. The method may include: specifying a number of zones K required for the polar grid partitioning and a number of angular segments M in a center region of the wafer; calculating a radial zone length L based on the number of zones specified; calculating an angular span $\theta_i$ for the $i^{th}$ radial zone, wherein i=1, 2, 3, ... K; and partitioning the wafer surface into a plurality of sites based on the radial zone length L and the angular span $\theta$ for each radial zone, wherein the plurality of sites have uniform site areas.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which:

FIG. 15A is an illustration depicting high order shape metrics obtained using a pixel-based shape-slope computation process;

FIG. 15B is an illustration depicting high order shape metrics obtained using a polynomial fitting process;

DETAILED DESCRIPTION

Reference will now be made in detail to the subject matter disclosed, which is illustrated in the accompanying drawings.

The present disclosure is directed to systems and methods for improved results of wafer higher order shape (HOS) characterization and wafer classification based on localized shapes. In accordance with the present disclosure, a wafer map is partitioned into a plurality of measurement site areas to improve the completeness of wafer shape representation. This method may therefore be referred to as the site based high order shape analysis method.

Figure 1:
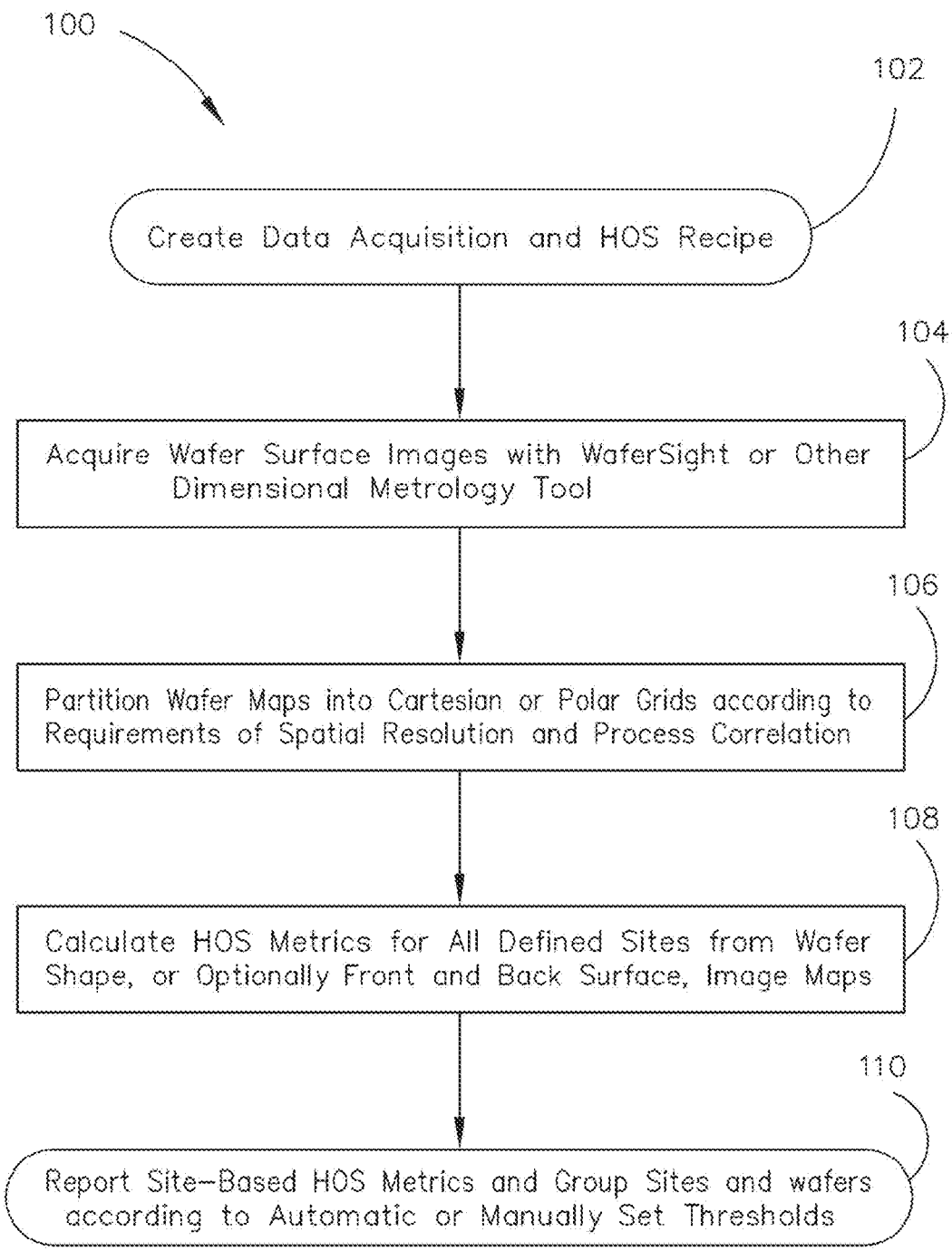
FIG. 1 is a flow diagram illustrating a site based high order shape analysis method.

FIG. 1 is a flow diagram illustrating the major steps of the site based high order shape analysis method 100 in accordance with the present disclosure. Data acquisition and HOS recipe may be created in step 102. Data acquisition and HOS recipe may specify how various wafer surface maps will be partitioned in later steps. Step 104 may acquire the wafer surface images directly utilizing wafer dimensional geometry tools such as the WaferSight metrology system from KLA-Tencor. It is contemplated, however, that the wafer shape image, wafer front and back surface shape images or the like may also be constructed indirectly using other metrology tools as well. Subsequently, step 106 may partition the wafer map into a plurality of measurement site areas and step 108 may calculate HOS metrics for each of the plurality of measurement site areas based on the wafer shape information (e.g., wafer shape, front and/or back surface, image maps or the like) obtained in step 104. Step 110 may then report the site based HOS metrics and may also group/classify sites and wafers according to automatic or manually set thresholds.

Figure 2:
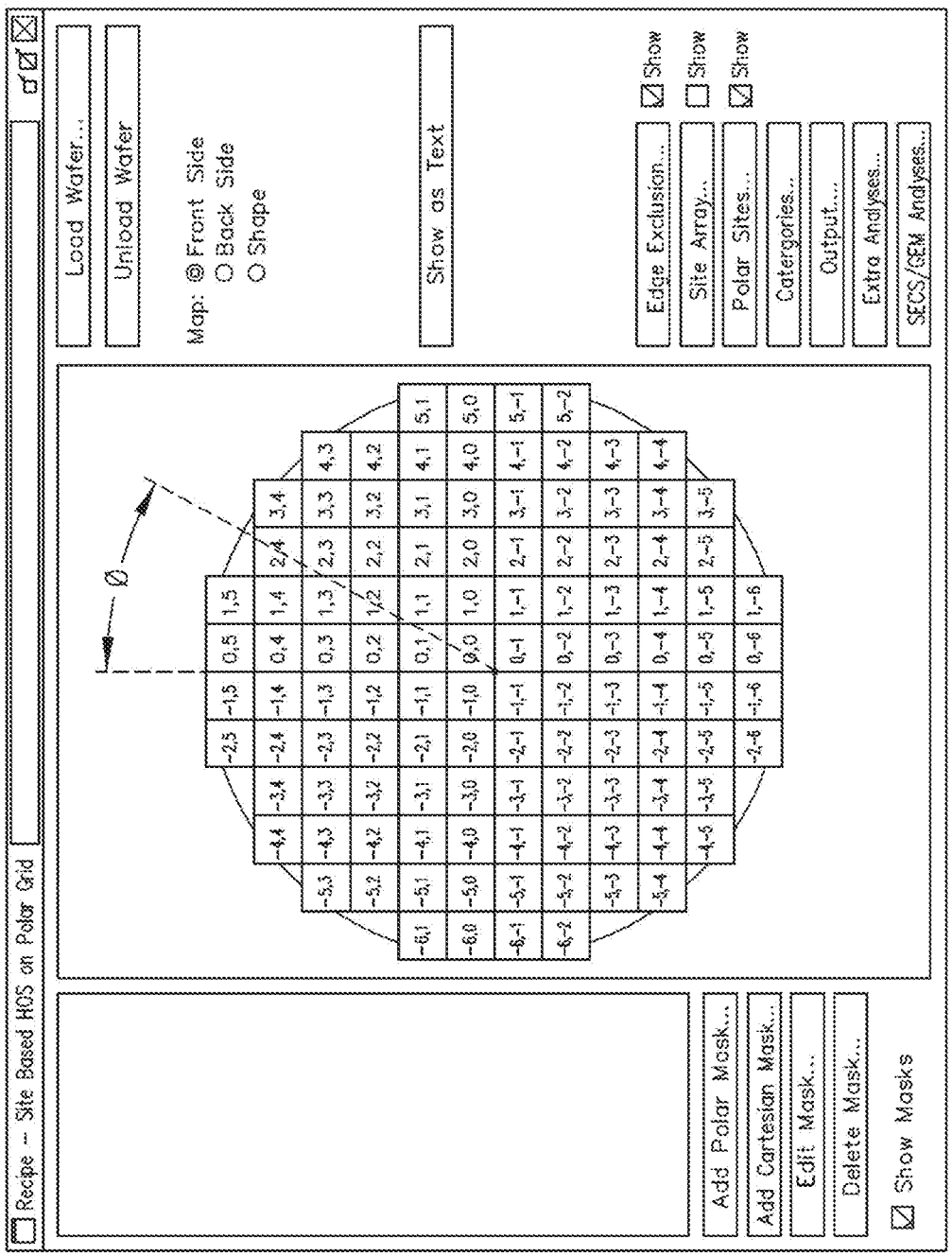
FIG. 2 is an illustration depicting a Cartesian grid partition scheme.

More particularly, the recipe for site based high order shape may be created based on Cartesian grid partition or polar grid partition. FIG. 2 is an illustration depicting a Cartesian grid partition. It is contemplated that different site sizes and shifts of the site array may be selected according to requirements of desired spatial resolution and alignment with other measurement or process setup. As illustrated in the figure, all sites in the Cartesian wafer surface partition have the same site area, except the partial sites at wafer edge regions.

Figure 3:
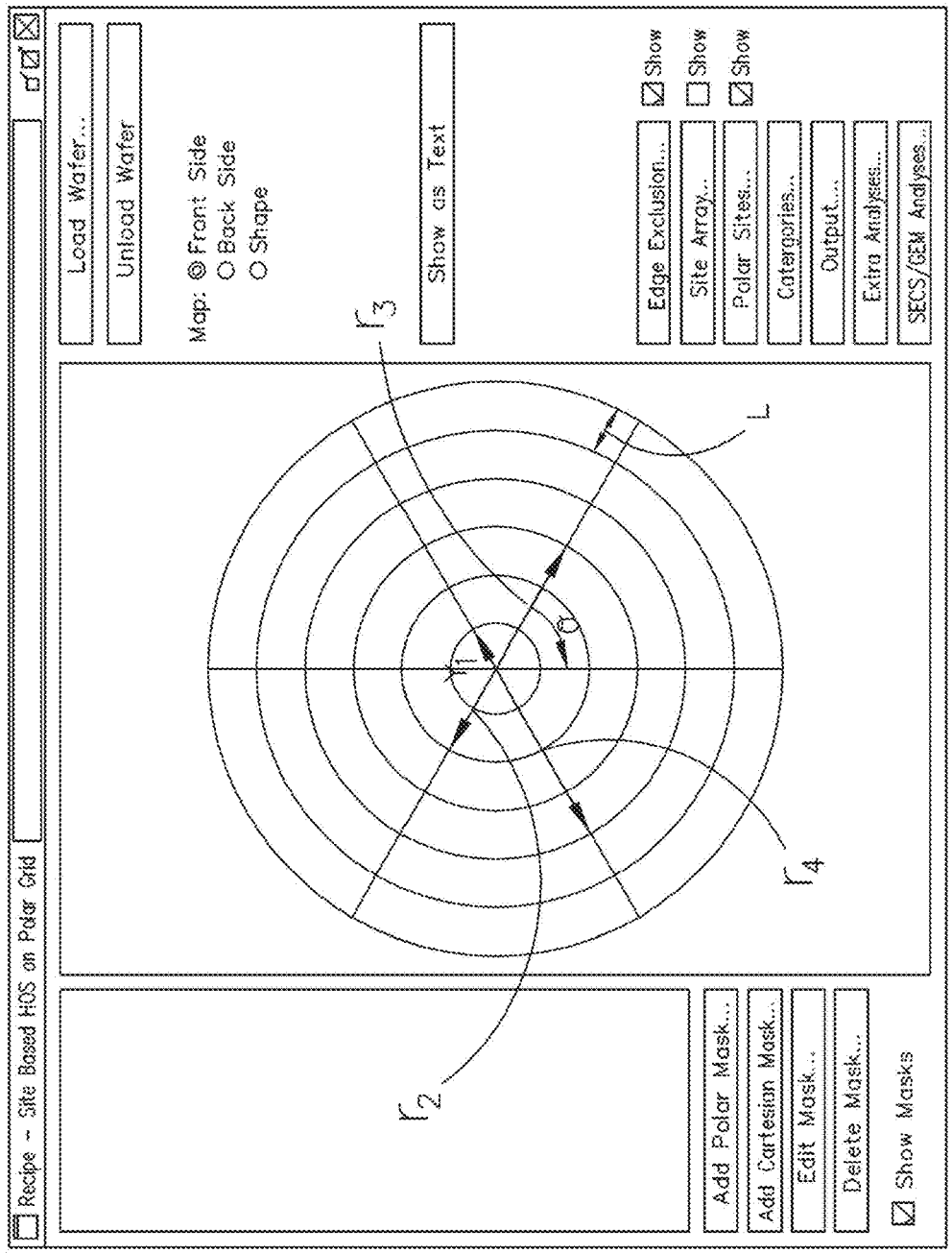
FIG. 3 is an illustration depicting a polar grid partition scheme.

Alternatively, the wafer surface may also be partitioned into polar grid for HOS analysis. Polar grid partition provides a better wafer edge region coverage. FIG. 3 is an illustration depicting an exemplary polar grid partition having 6 zones and 6 sectors. In this partition scheme, all polar sites have the same radial zone length L and the same sector angular span θ. The zone boundaries of the $i^{th}$ zone may be determined by equation:

$$r_i = iL \text{ and } r_{i-1} = (i-1)L, \ i=1,2,3,\ldots K$$

For instance, the first zone is a circular-shaped zone with radius $r_1=L$, the second zone is a ring-shaped zone defined by an outer region having an outer radius $r_2=2L$ and excluding an inner region having an inner radius $r_1=L$ and so on. Furthermore, the area A of the polar site may be determined by equation:

$$A_i = \frac{\theta}{2}(r_i^2 - r_{i-1}^2) = \frac{\theta}{2}(i^2 - (i-1)^2)L^2, \ i=1,2,3,\ldots K$$

where K is the number of zones in the polar partition and KL=R is the wafer radius.

While this exemplary polar grid partition may be utilized for HOS analysis, it is clear that the site areas defined by this partition scheme may vary greatly. For example, in the scheme shown in FIG. 3, the ratio of the site areas in the wafer edge and in the wafer center is 11. Such variations in site areas can result in the big spread in the HOS measurement values and affect the accurate wafer shape characterization.

The present disclosure therefore provides new polar grid partition schemes that are able to partition the wafer surface into uniform areas. The first polar grid partition scheme in accordance with the present disclosure adopts the non-uniform radial span and defines the partition and defines the site zone boundaries of the $i^{th}$ zone as:

$$r_i = \sqrt{i}L \text{ and } r_{i-1} = \sqrt{i-1}L, \; i=1,2,3,\ldots K$$

where L is determined by the wafer radius R and the maximum zone number K in the partition as:

$$L = \frac{R}{\sqrt{K}}$$

Figure 4:
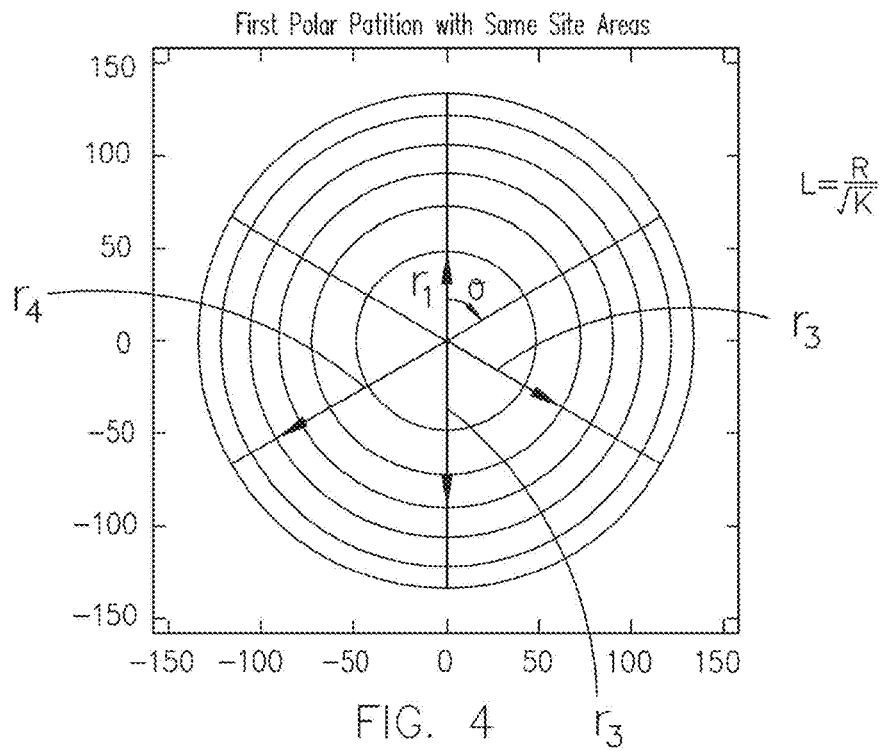
FIG. 4 is an illustration depicting a polar grid partition scheme configured for providing uniform measurement site areas.

In accordance with the polar grid partition scheme described above, the sector angular span θ remains constant and the radial span for each zone may vary to keep the site areas uniform. For example, for the same numbers of the sectors and zones as depicted in FIG. 3, the polar sites created according to this new partition scheme are illustrated in FIG. 4. It is noted that all polar sites now have the same areas and can be used to improve the accuracy of the wafer shape analysis.

Alternatively, the second polar grid partition scheme in accordance with the present disclosure may adjust the angular span θ of the site in each zone radius to obtain the uniform site area while keeping the radial length constant. In this case, the angular span for the $i^{th}$ radial zone band may be determined utilizing equation:

$$\theta_i = \frac{1}{2i-1}\frac{2\pi}{M}, \; i=1,2,3,\ldots K$$

where M is the number of the angular segments in the wafer center region (identified as region 502 in FIG. 5) and K is the number of the zones.

Figure 5:
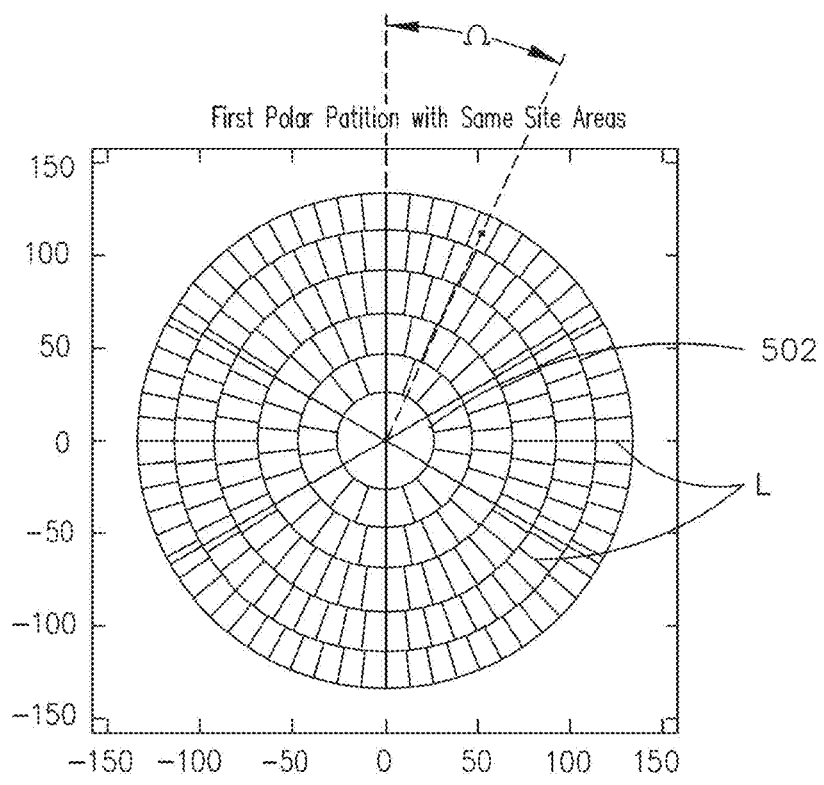
FIG. 5 is an illustration depicting another polar grid partition scheme configured for providing uniform measurement site areas.

Using the second partition scheme for the case M=6 and K=6, the polar site partition with uniform site areas can be obtained as shown in FIG. 5, which has good wafer edge region coverage, good site spatial resolution and provides area uniformity.

It is contemplated that similar to the two schemes described above where uniform site area is maintained by either keeping the radial length constant and varying the angular span or vice-versa, uniform site area polar partition may also be obtained by varying both the radial length and the angular span simultaneously. Furthermore, the polar grid partitions having 6 zones and 6 sectors as described in the example above are used merely for illustrative purposes. It is contemplated that the number of zones and the number of sectors may vary without departing from the spirit and scope of the present disclosure.

Figure 6:
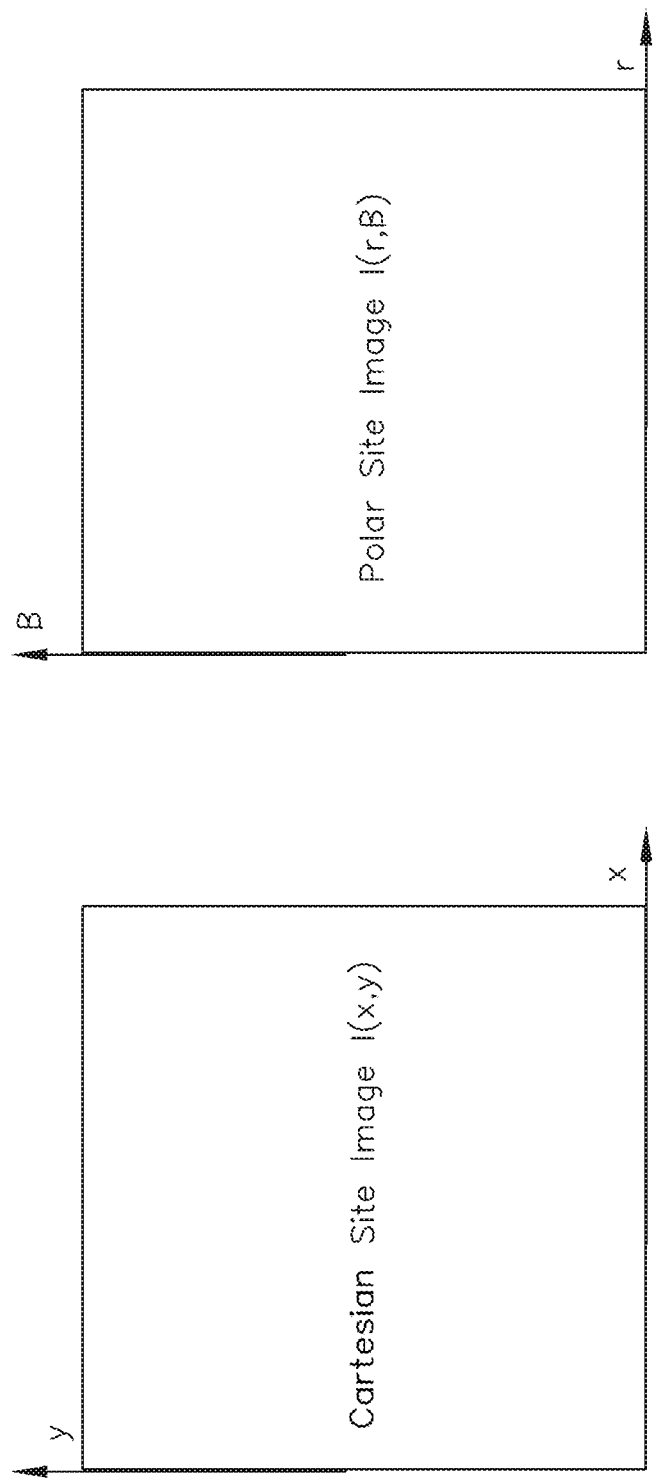
FIG. 6 is an illustration depicting site image shape data obtained for each measurement site.

As illustrated in FIG. 1, once the wafer map is partitioned and the wafer shape information is obtained, step 108 may calculate HOS metrics for each of the plurality of uniform measurement site areas based on the obtained wafer shape information. More specifically, given the site image shape data, I(x,y), in the Cartesian wafer partition as shown in FIG. 6, the following best fitting surfaces of orders 0 to 2 may be calculated as defined by the following three equations, where N is the number of valid pixels in the given site image and the surface coefficients C(i,j) in these equations may be determined by the least mean squared error (LMS) method. For instance, the mean level of site image may be calculated as:

$$L_c = \sum_{(x,y)} \frac{I(x,y)}{N}$$

In addition, the first order best-fit surface of site image may be calculated as:

$$P_c(x,y) = C(0,0) + C(1,0)x + C(0,1)y$$

And the second order best-fit surface of site image may be calculated as:

$$S_c(x,y) = C(0,0) + C(1,0)x + C(0,1)y + C(2,0)x^2 + C(1,1)xy + C(0,2)y^2$$

It is contemplated that higher order best-fit surface of site image (order greater than 2) may be calculated to characterize the complex wafer surface geometry. In addition, the corresponding non-correctable shape components for different surface fitting orders may also be computed to correlate to higher order process parameters.

For example, the deviations of the input site image, I(x,y), from the site level $L_c$ and two best fit surfaces, $P_c(x,y)$ and $S_c(x,y)$, may be calculated as:

$$D_0(x,y) = I(x,y) - L_c$$

$$D_1(x,y) = I(x,y) - P_c(x,y)$$

$$D_2(x,y) = I(x,y) - S_c(x,y)$$

These deviation images ($D_0$, $D_1$ and $D_2$) are obtained by subtracting the polynomial-fit surface from the original surface of each measurement site. They represent the higher order shape components which cannot be described by the corresponding zero order, first order and second order surface equations, and therefore cannot be corrected by the corresponding zero order, first order and second order surface correction processes. These various deviation metrics may also be referred to as residues or shape residues, and various deviations/residues may be obtained by varying the order of the fitting polynomial. Together with the surface coefficients, these deviation images provide rich information about the wafer shape and can be used to characterize and sort the wafers effectively.

For instance, wafer shape information (may be referred to as surface shape metrics) that can be calculated for each measurement site based on the surface coefficients may include: X Slope=C(1,0), which represents the average site image slope in x direction with unit nm/mm; Y Slope=C(0,1), which represents the average site image slope in y direction with unit nm/mm;

$$T_1 = \sqrt[2]{C^2(1,0) + C^2(0,1)},$$

which represents the magnitude of the site image slope with unit nm/mm; and $$T_2 = \sqrt[2]{C^2(2,0) + C^2(1,1) + C^2(0,2)},$$

which represents the magnitude of the second order surface components with unit nm/mm$^2$. It is noted that the magnitude of the first order polynomial fit coefficients is the magnitude of the shape-slope, and the magnitude of the second order polynomial fit coefficients is the magnitude of shape-curvature or simply shape-curvature. It is contemplated that magnitude of other higher-order polynomial fit coefficients may be derived in a similar manner.

Additional site slope metrics may also be derived from the surface coefficients and the site position angle Ø (as depicted in FIG. 2) determined by the site center position on the wafer surface. For instance, the radial slope of the measurement site may be calculated as Radial Slope=C(1,0)×cos(Ø)+C(0,1)×sin(Ø) with unit nm/mm, and the tangential slope of the measurement site may be calculated as Tangential Slope=−C(1,0)×sin(Ø)+C(0,1)×cos(Ø) with unit nm/mm.

While the magnitudes of the shape slope and the shape curvature are defined in equations above, it is contemplated that if more detailed second order shape components are required, they may be obtained from the three surface components C(2,0), C(1,1) and C(0,2), which provide the second order shape curvature descriptions about the local shape. For instance, the curvature in x direction may be obtained as X Curvature=C(2,0), the curvature in y direction may be obtained as Y Curvature=C(0,2), and the curvature in the (x=y) direction may be obtained as XY Curvature=C(1,1).

Furthermore, the following deviation metrics may also be constructed from the deviation images with unit nm:

$$PD_0 = \max[D_0(x, y)]; VD_0 = \min[D_0(x, y)];$$

$$PVD_0 = PD_0 - VD_0; MD_0 = \sum_{(x,y)} \frac{|D_0(x, y)|}{N}$$

$$PD_1 = \max[D_1(x, y)]; VD_1 = \min[D_1(x, y)];$$

$$PVD_1 = PD_1 - VD_1; MD_1 = \sum_{(x,y)} |D_1(x, y)|/N$$

$$PD_2 = \max[D_2(x, y)]; VD_2 = \min[D_2(x, y)];$$

$$PVD_2 = PD_2 - VD_2; MD_2 = \sum_{(x,y)} |D_2(x, y)|/N$$

It is contemplated that these deviation metrics provide the information about the wafer shape after certain correction procedures. For example, the metric $PD_0$ tells the maximum positive error after the site leveling operation, the metric $MD_1$ denotes the average deviation error after the piston/tilt correction, which may be carried out by the stepper/scanner in auto-focus process, and $MD_2$ gives the information about the surface components higher than the second order.

Figure 7:
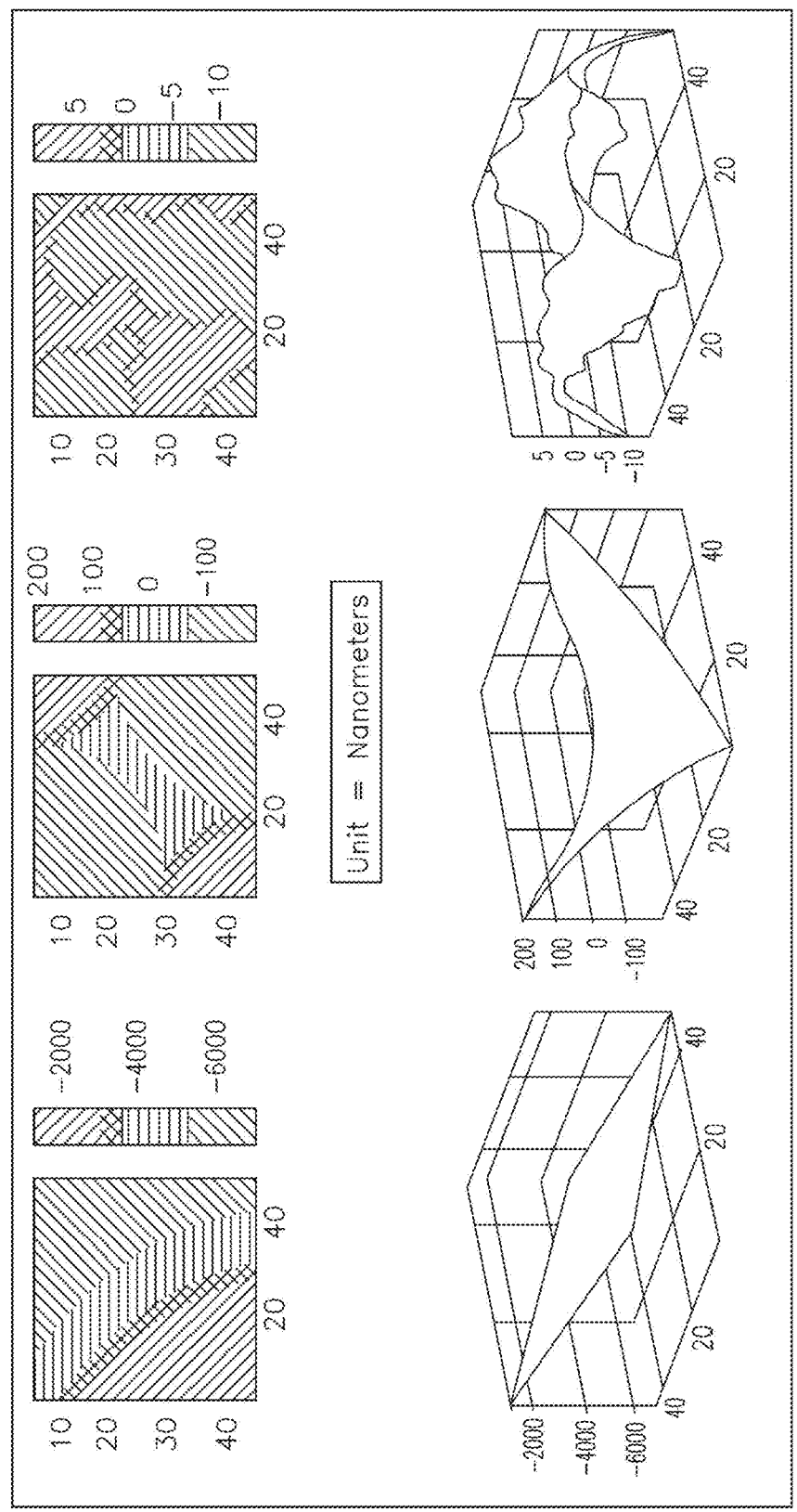
FIG. 7 is an illustration depicting a site shape image, two surface fitting images and the corresponding deviation (residue) images.

FIG. 7 illustrates one original site shape image I(x,y) and its corresponding two deviation images $D_1(x,y)$ and $D_2(x,y)$ where the distributions of the shape components in the original shape image can be clearly seen from two deviation images. It is noted that if the original shape image has only shape components of the first order, $D_1(x,y)$ will be an all zero plane. Similarly, if the original image has only the shape components up to the second order, then the second order deviation image $D_2(x,y)$ will be an all zero plane.

Figure 8B:
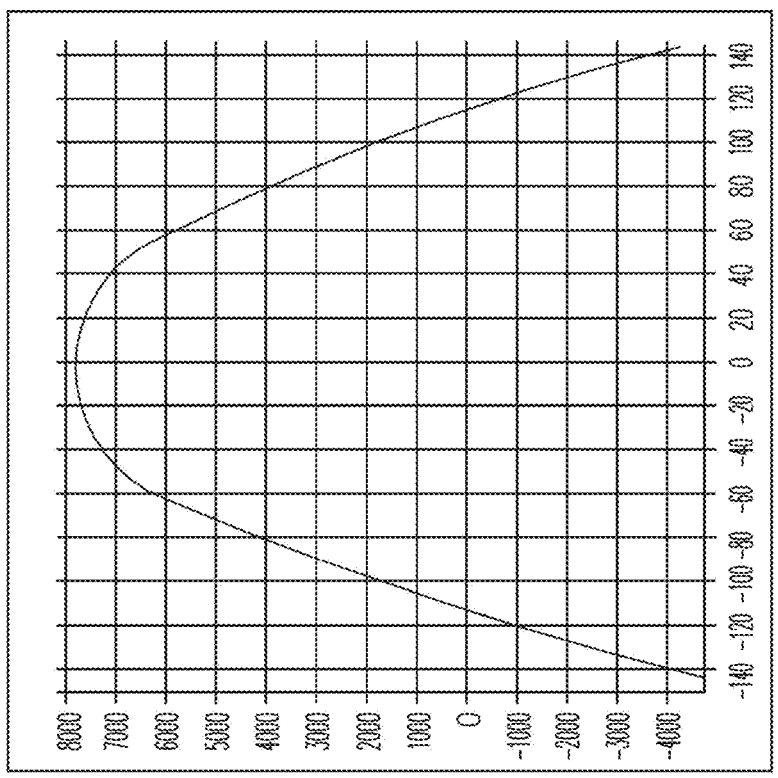
FIG. 8B is an illustration depicting the X profile of the exemplary wafer shape image of FIG. 8A.
Figure 8A:
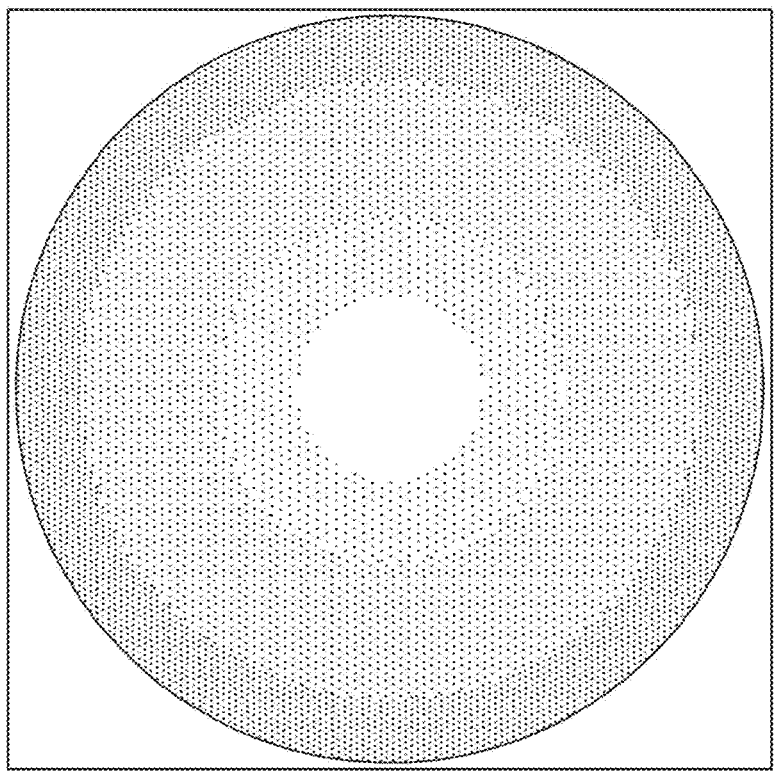
FIG. 8A is an illustration depicting an exemplary wafer shape image.
Figure 9:
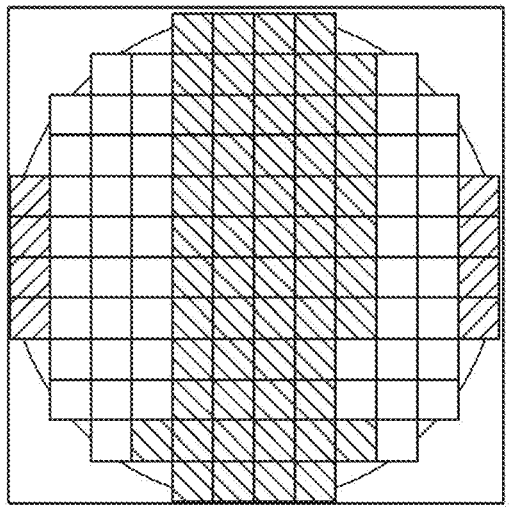
FIG. 9 are illustrations depicting various graphical representations of the site based high order shape analysis in accordance with the present disclosure.
Figure 9:
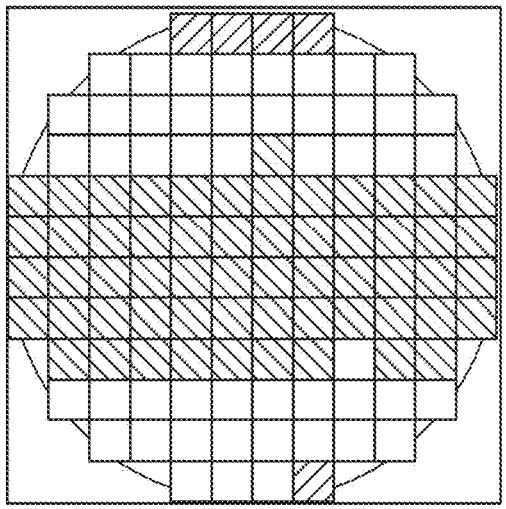
Figure 9:
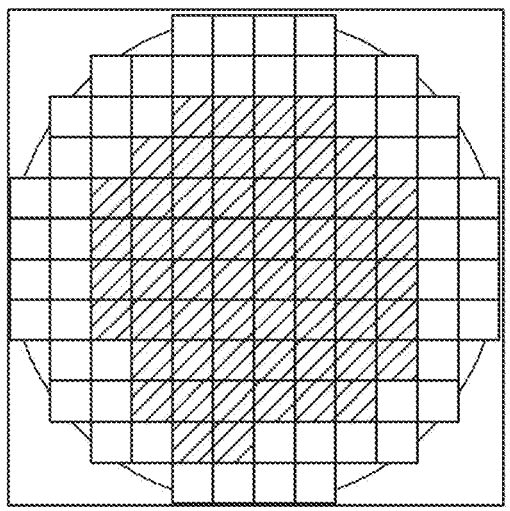
Figure 9:
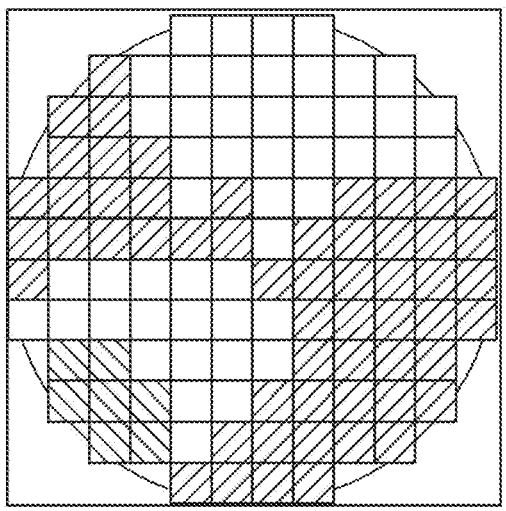

It is contemplated that the HOS metrics calculated for each of the measurement site areas in step 108 may be utilized to group/classify the site areas for reporting purposes in step 110. In addition, automatic or manually set thresholds may be utilized to visualize the site based high order shape analysis results. For example, FIGS. 8A-8B show a wafer shape image and its X profile. This wafer has high shape slope at the wafer edge region and has higher order components than linear terms at the wafer radius of 40 mm region. The X slope metric map, the Y slope metric map, the radial slope map and the tangential slope map may be calculated according to the equations described above and the calculated site metric values may be presented for each measurement site in a corresponding map as shown in FIG. 9. Alternatively/additionally, the calculated shape metrics and the classification results may also be reported in measurement result files (e.g., a text-based or machine-readable result file).

In the maps shown in FIG. 9, each site may be shaded (or colored based on the specific implementation) according to the calculated site metric values and shading/coloring rules. For instance, a site may be shaded/colored in a first manner if its metric value is below a lower threshold, in a second manner if its metric value is between the lower threshold and an upper threshold, or in a third manner if its metric value is above the upper threshold. It is contemplated that the lower and upper thresholds may be set manually by the user to classify the sites and wafers. Alternatively, the thresholds may be determined automatically. For instance, a median value of absolute metric values of all sites may be calculated first and used as the lower threshold. The upper threshold may be defined subsequently as twice the lower threshold. It is understood, however, that utilizing two thresholds is merely exemplary. The number of thresholds utilized for grouping/classifying the measurement sites may vary without departing from the spirit and scope of the present disclosure. Furthermore, the threshold values may also be determined differently as described above.

Figure 10B:
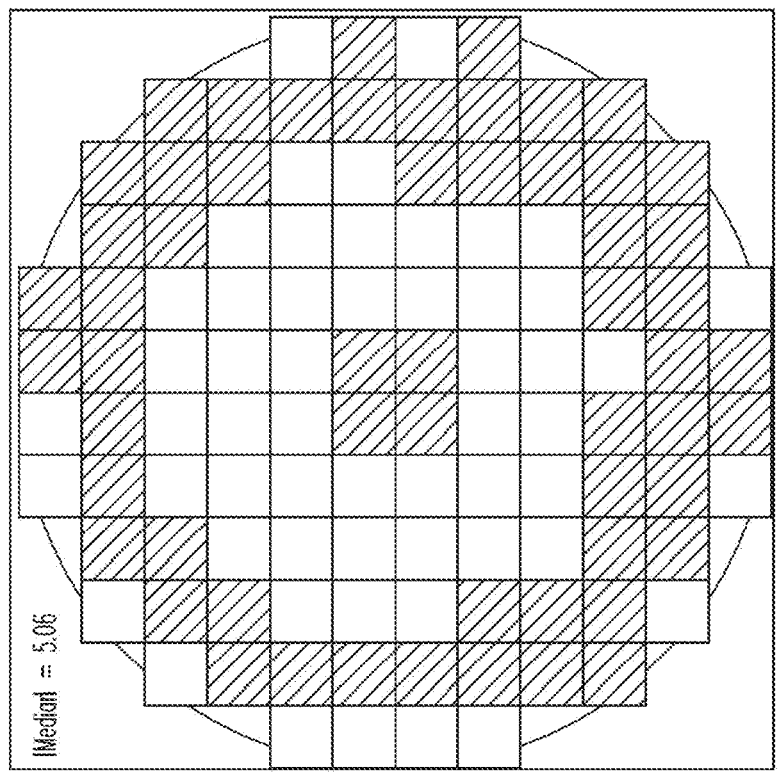
FIG. 10B is an illustration depicting a second order coefficient derived map for site based high order shape analysis.
Figure 10A:
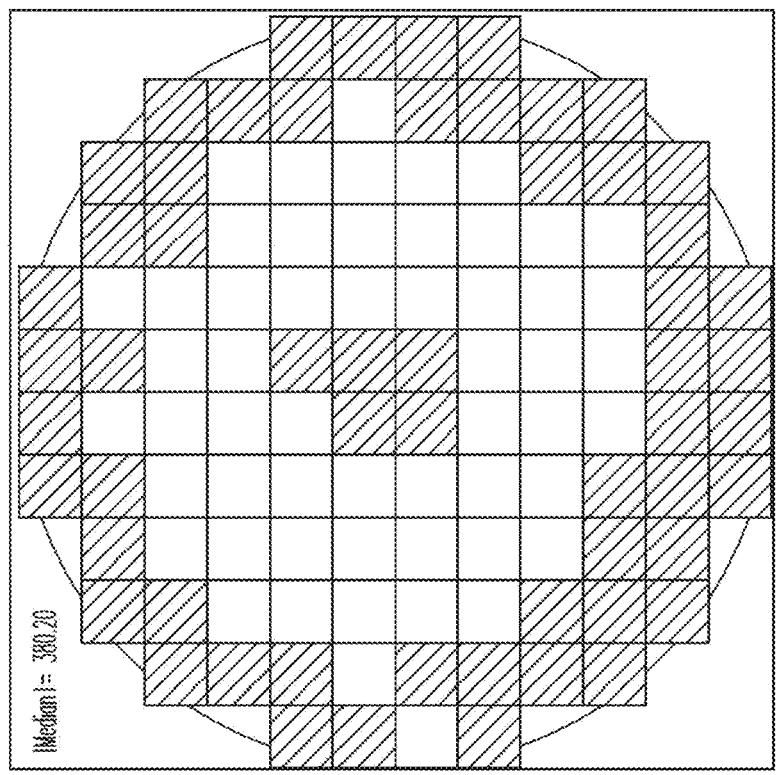
FIG. 10A is an illustration depicting a deviation map for site based high order shape analysis.

It is clear that the four slope maps shown in FIG. 9 describe the wafer shape slope in different orientations and provide comprehensive wafer shape information. The radial slope map and the tangential slope map indicate that wafer shape a has bigger slope in the wafer edge region than the interior region and that the wafer shape has very smooth shape profile in the tangential direction. Furthermore, to obtain shape information of higher order components, the metrics from the first order deviation map, such as $PVD_1$, or the metrics from the second order fitting coefficients, such as $T_2$, may be utilized. FIGS. 10A-10B show the deviation $PVD_1$ map and the second order coefficient derived $T_2$ map. Both of them characterize the wafer shape components higher than the first order and they both show that there are bigger higher order components in wafer radius of 40 mm neighborhood region. $T_2$ metric map also indicates that there are higher order shape components in wafer edge sites.

Figure 11B:
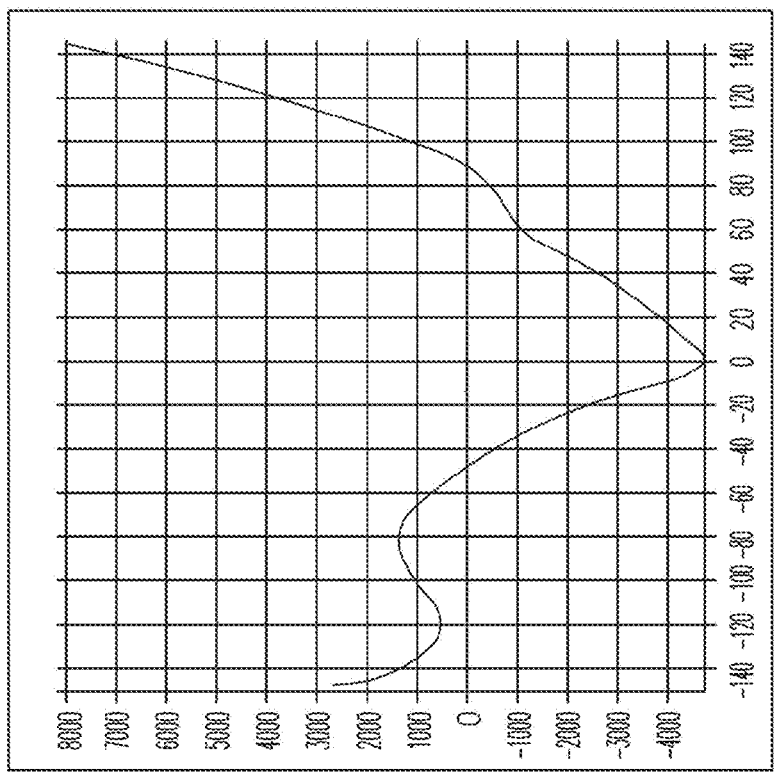
FIG. 11B is an illustration depicting the profile of the exemplary wafer shape image of FIG. 11A in −45° orientation.
Figure 11A:
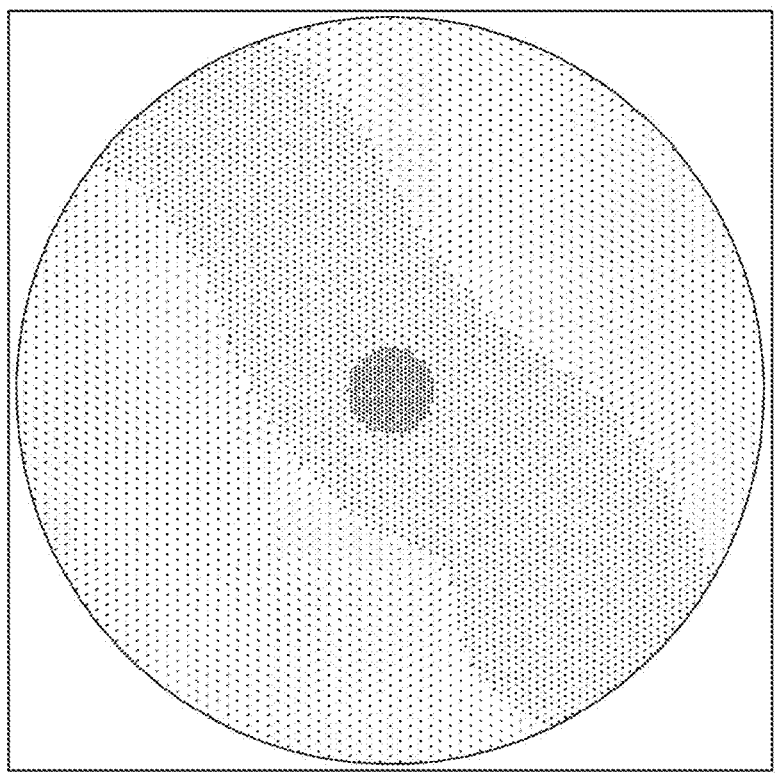
FIG. 11A is an illustration depicting another exemplary wafer shape image.
Figure 12:
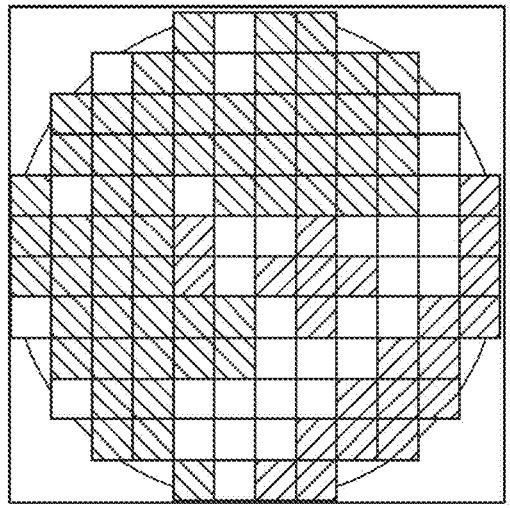
FIGS. 12-13 are illustrations depicting various graphical representations of the site based high order shape analysis in accordance with the present disclosure.
Figure 12:
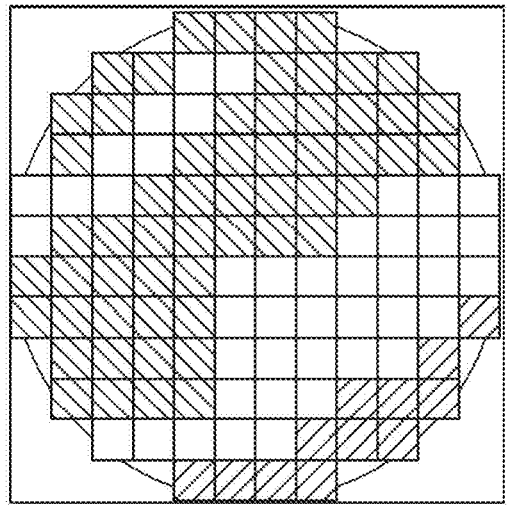
Figure 12:
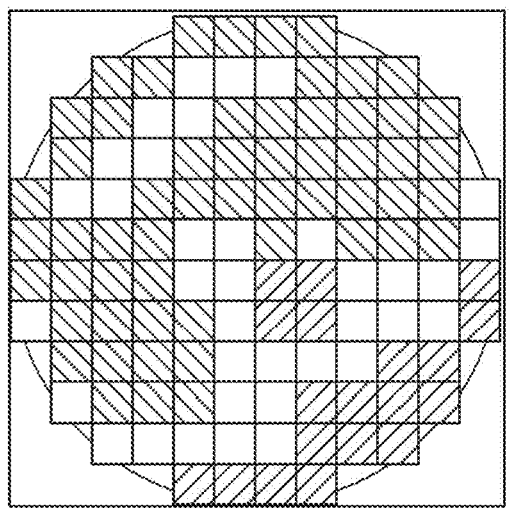
Figure 12:
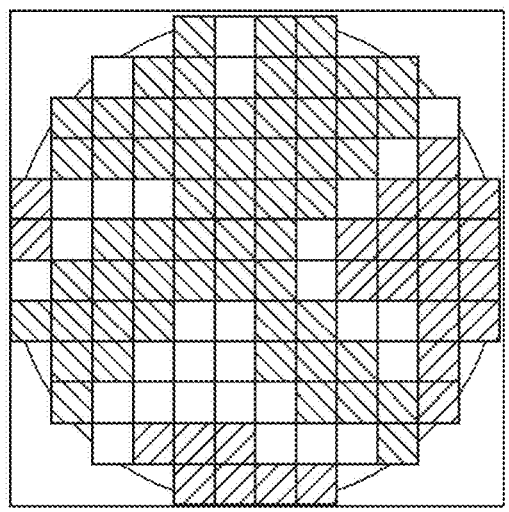
Figure 13:
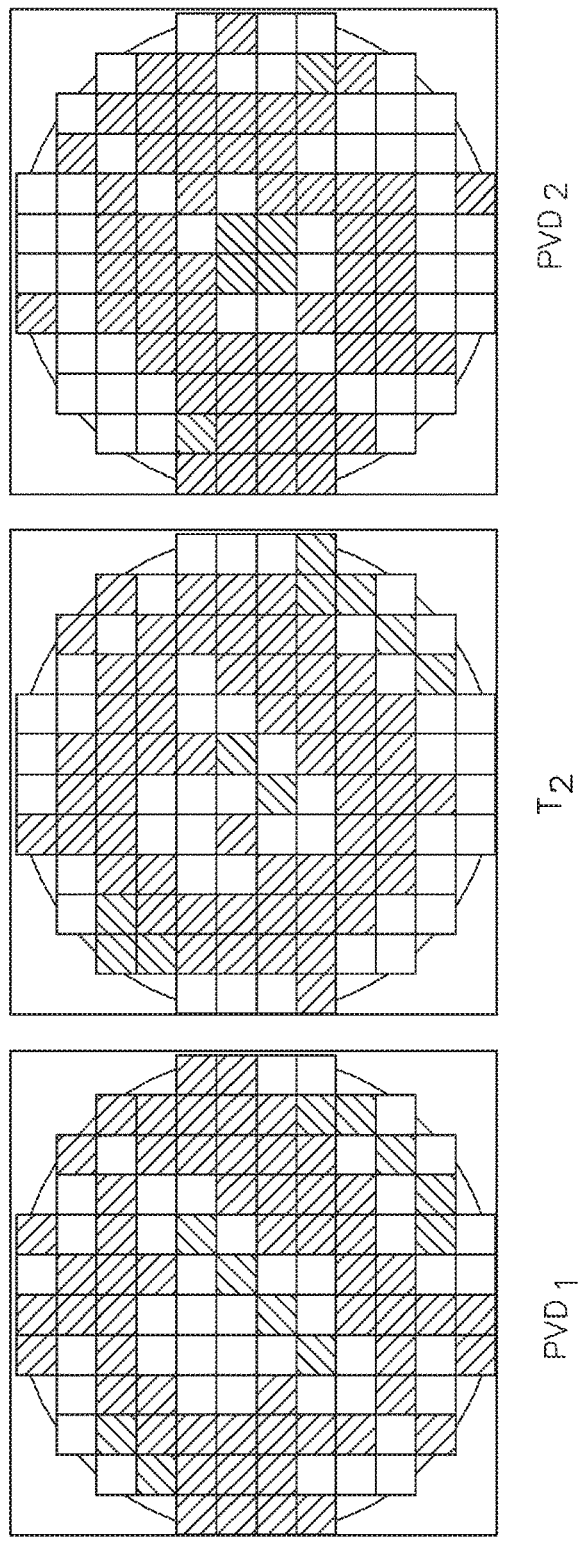

FIGS. 11A-11B show another exemplary wafer shape image and its profile in −45° orientation. The corresponding four slope metric maps are shown in FIG. 12. As indicated in FIG. 12, the high shape slope in the south-east wafer edge region is well detected by these slope metric maps. In addition, the tangential slope map shows that this wafer has higher tangential slope components in the 3 o'clock and 6 o'clock wafer edge regions than other wafer edge regions. Furthermore, FIG. 13 shows the $PVD_1$ map, $T_2$ map and $PVD_2$ map, where the $PVD_2$ map clearly shows that the deep shape valley in the wafer center region has the shape components higher than the second order. It is contemplated that providing the ability for the user to visualize the information as depicted in FIGS. 12 and 13 is appreciated in various situations. However, it is also contemplated that such information may be reported in a classification result file (e.g., a text-based or machine-readable result file) without departing from the spirit and scope of the present disclosure.

While the surface fitting coefficients and deviation images discussed above are defined on the Cartesian (x,y) image site partitions, the principles and methods can be extended to polar (r,β) partitions as well. For instance, if polar position is used for the HOS characterization, the acquired wafer image maps (usually in Cartesian space) may be converted/transformed into polar space first. The entire wafer polar image may then be partitioned into rectangular polar space data blocks I(r,β), as shown in FIG. 6. The boundaries of these polar space data blocks are defined by the particular partition scheme selected (e.g., from the schemes described in FIG. 3, 4 or 5). That is, the polar site image in FIG. 6 corresponds to a site area in FIG. 3, 4 or 5 based on the partition scheme selected, and the polar sites shown in Cartesian space in FIGS. 3, 4 and 5 becomes rectangular data blocks in the polar space depicted in FIG. 6.

The surface fitting and deviation image calculation may now be calculated as follows:

$$L_p = \sum_{(r,\beta)} \frac{I(r,\beta)}{N}$$

$$P_p(r,\beta) = C(0,0) + C(1,0)r + C(0,1)\beta$$

$$S_p(r,\beta) = C(0,0) + C(1,0)r + C(0,1)\beta + C(2,0)r^2 + C(1,1)r\beta + C(0,2)\beta^2$$

Similarly, the deviations of the input site image, I(r,β), from the site level $L_p$ and two best fit surfaces, $P_p(x,y)$ and $S_p(r,\beta)$, may be calculated as:

$$D_0(r,\beta) = I(r,\beta) - L_p$$

$$D_1(r,\beta) = I(r,\beta) - P_p(r,\beta)$$

$$D_2(r,\beta) = I(r,\beta) - S_p(r,\beta)$$

Additional site slope metrics may also be derived from the surface coefficients. For instance, the radial slope of the measurement site may be calculated as Radial Slope=C(1,0), which represents the average site image shape slope in r direction, and the tangential slope of the measurement site may be calculated as Tangential Slope=C(0,1), which represents the average site image shape slope in β direction. Furthermore, the X shape slope and Y shape slope values in the polar space partition may be calculated from the radial shape slope, tangential shape slope and the site center angle Ω (as depicted in FIG. 5). For instance, the X shape slope may be calculated as X Slope=Radial Slope*cos(Ω)−Tangential Slope*sin(Ω) and the Y shape slope may be calculated as Y Slope=Radial Slope*sin(Ω)+Tangential Slope*cos(Ω). Other metrics such as $T_1$ and $T_2$ may also be calculated in a similar manner as described above. $T_1$ and $T_2$ provide the magnitude of the shape slope and the magnitude of the second order shape components or shape curvature components.

Figure 14:
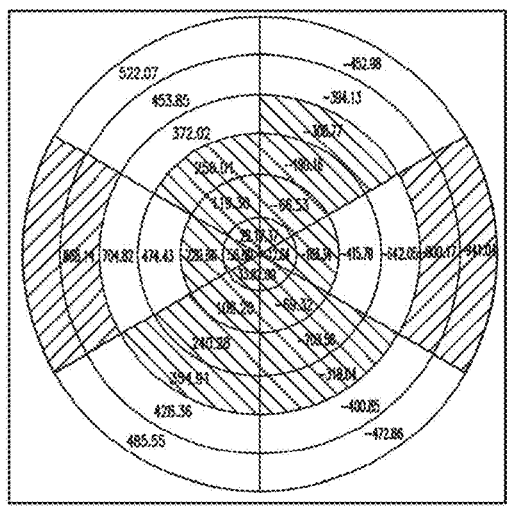
FIG. 14 is an illustration depicting various graphical representations of the site based high order shape analysis, presented in polar space, in accordance with the present disclosure.
Figure 14:
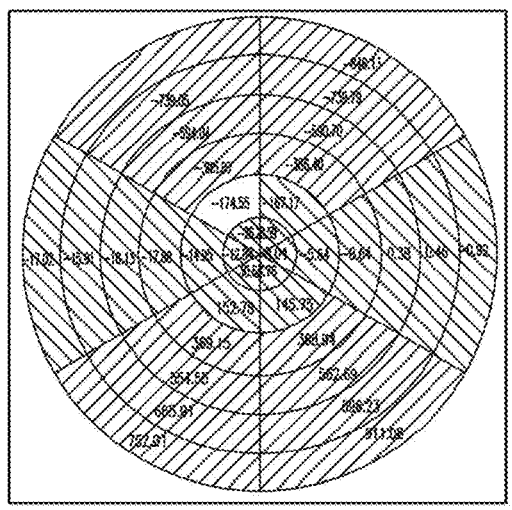
Figure 14:
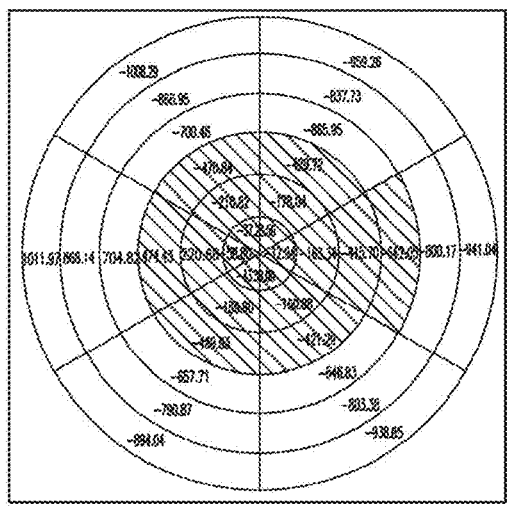
Figure 14:
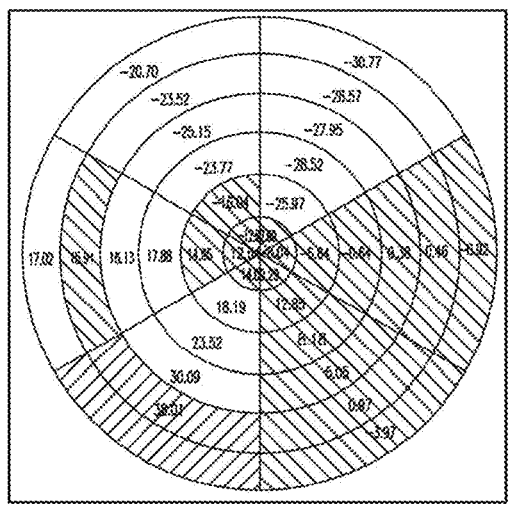

Similar to the Cartesian space described above, the HOS metrics calculated for each of the measurement site areas in the polar space may also be utilized to group/classify the site areas for reporting purposes. For example, FIG. 14 shows the X slope metric map, the Y slope metric map, the radial slope map and the tangential slope map for an exemplary wafer partitioned utilizing polar partitioning. It is understood that the polar space partitioning scheme depicted in FIG. 14 is merely exemplary. The uniform site area partitioning scheme depicted in FIGS. 4 and 5 may also be utilized for reporting purposes without departing from the spirit and scope of the present disclosure. Furthermore, it is contemplated that polar partition may provide better wafer shape characterization and better correlation with the process information in certain applications.

Alternative to calculating the HOS metrics based on fitting first order polynomials across sites/polar-sectors as described above, another technique for shape slope computation is to compute the X slope, the Y slope, the radial slope and the tangential slope (may be jointly referred to as x/y/radial/tangential components) at every pixel location via numerical methods such as forward difference, backward difference, and central difference methods. For instance, subsequently to capture local shape-slope effects efficiently and report to the user in the form of images and text-based data output, the pixel-based shape-slope maps (x/y/radial/tangential components) may be segmented into sites/polar-sectors and a mean value of shape-slopes (x/y/radial/tangential components) may be reported for each site/polar-sector. Similarly max/min/range and other values may be reported per site/polar-sector. For illustration purpose a contour image of the mean radial shape slope for a wafer segmented by sites is shown in FIG. 15A. This is also compared to slope computation by way of polynomial fitting described earlier in and as shown in FIG. 15B.

It is observed that the two methods of slope computation (i.e., based on fitting first order polynomials, or alternatively, based on numerical methods) produce very similar results. It is therefore contemplated that step 108 may utilize either method to calculate metrics for the measurement sites. It is further contemplated that other alternative computation methods may also be utilized to compute the various metrics described above. The specific equations and/or method utilized may vary without departing from the spirit and scope of the present disclosure.

It is also observed that the metrics described above provide metric values for each field/site. These metric values by definition are suitable for performing inter-field (field-to-field variations) data analysis, but may not be optimal for performing intra-field (within field variations) data analysis. It is contemplated, however, that the method in accordance with the present disclosure may be adapted to provide metrics for multiple data points (may be referred to as targets) per measurement site. Providing metrics for multiple data points for each site will therefore support intra-field data analysis, which may be appreciated in various wafer measurement applications.

Figure 16:
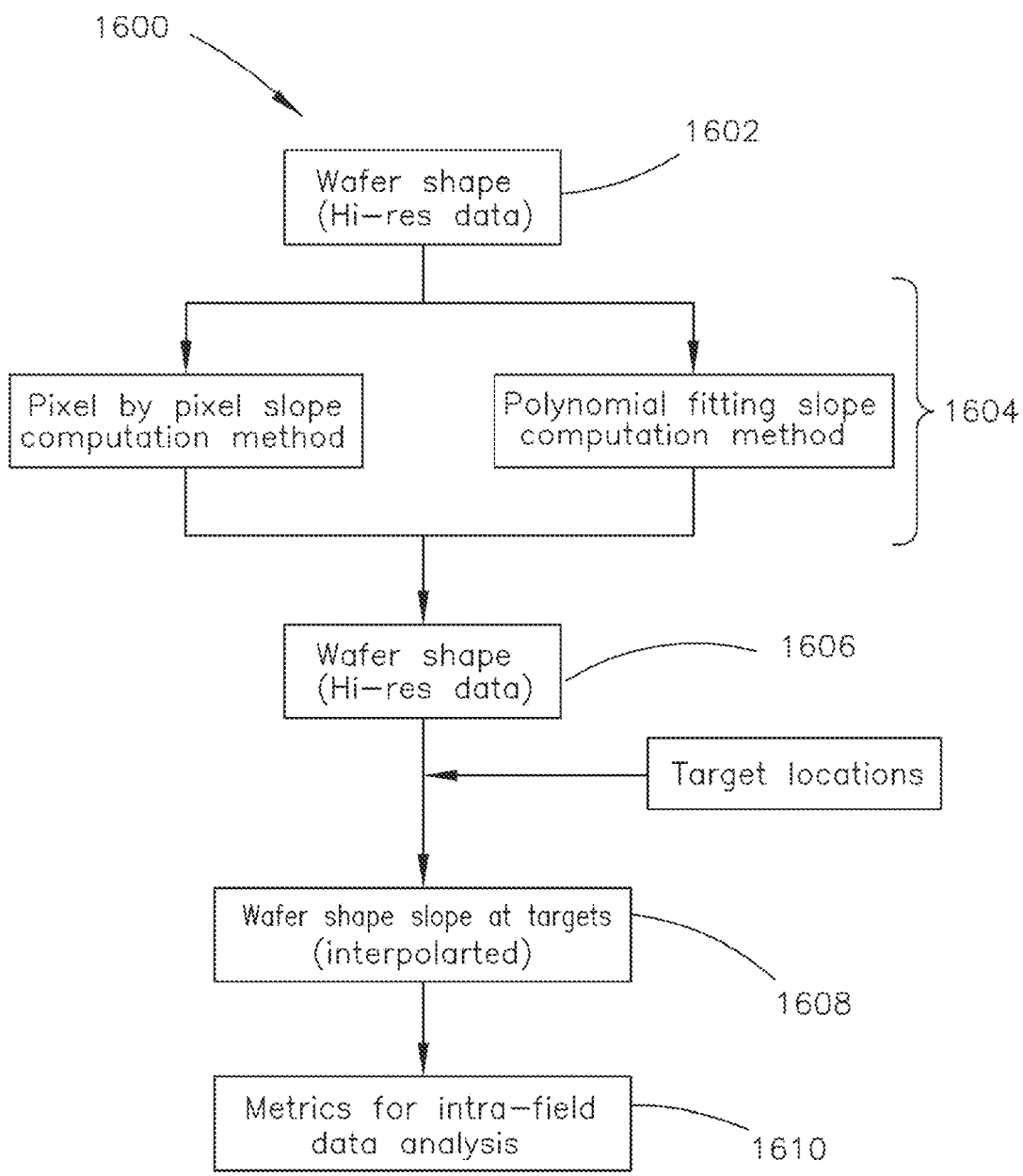
FIG. 16 is a flow diagram illustrating an intra-field data analysis method.
Figure 17:
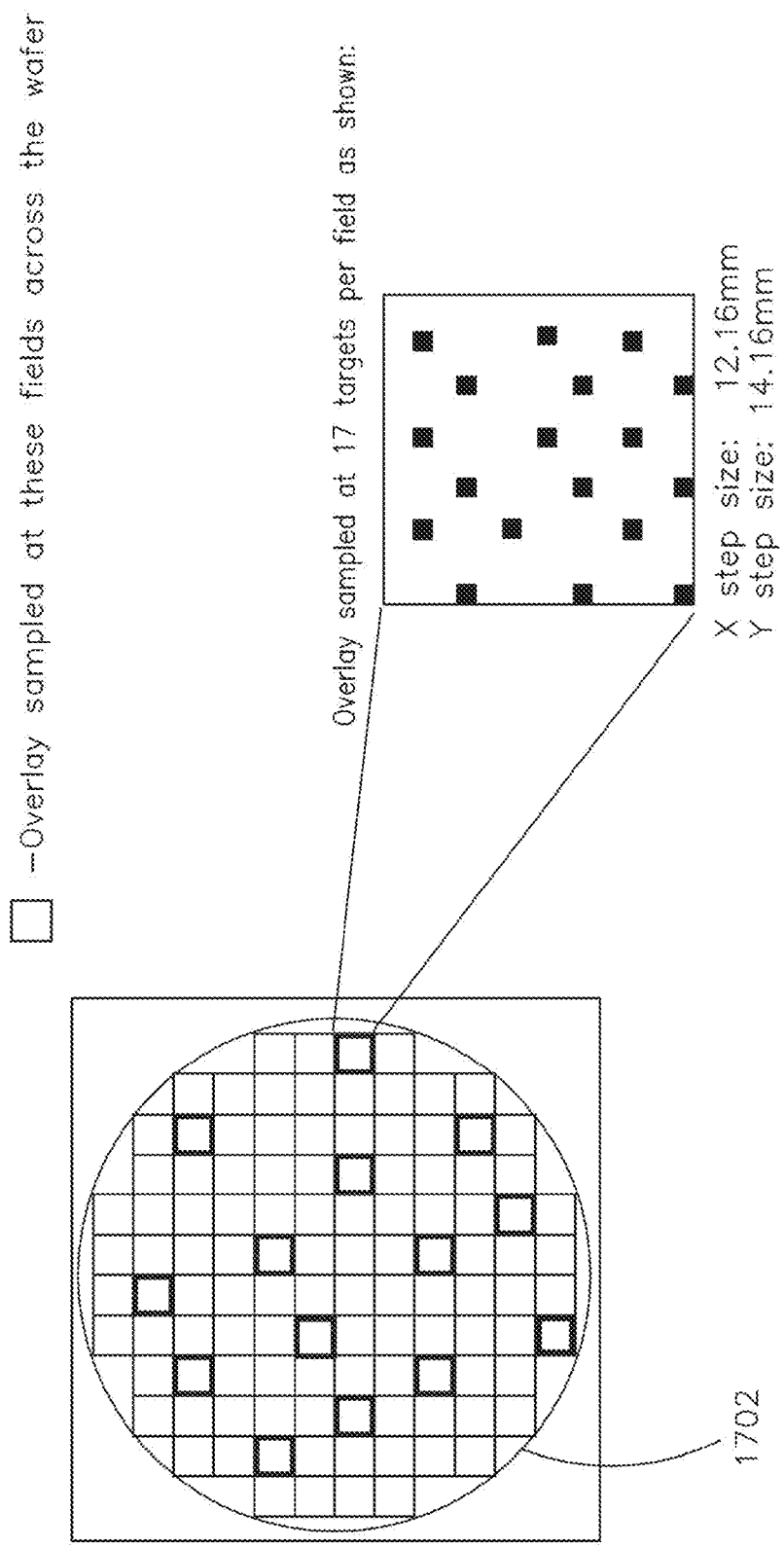
FIG. 17 is an illustration depicting a number of predetermined target locations within a lithography field and across multiple fields within a wafer.
Figure 18:
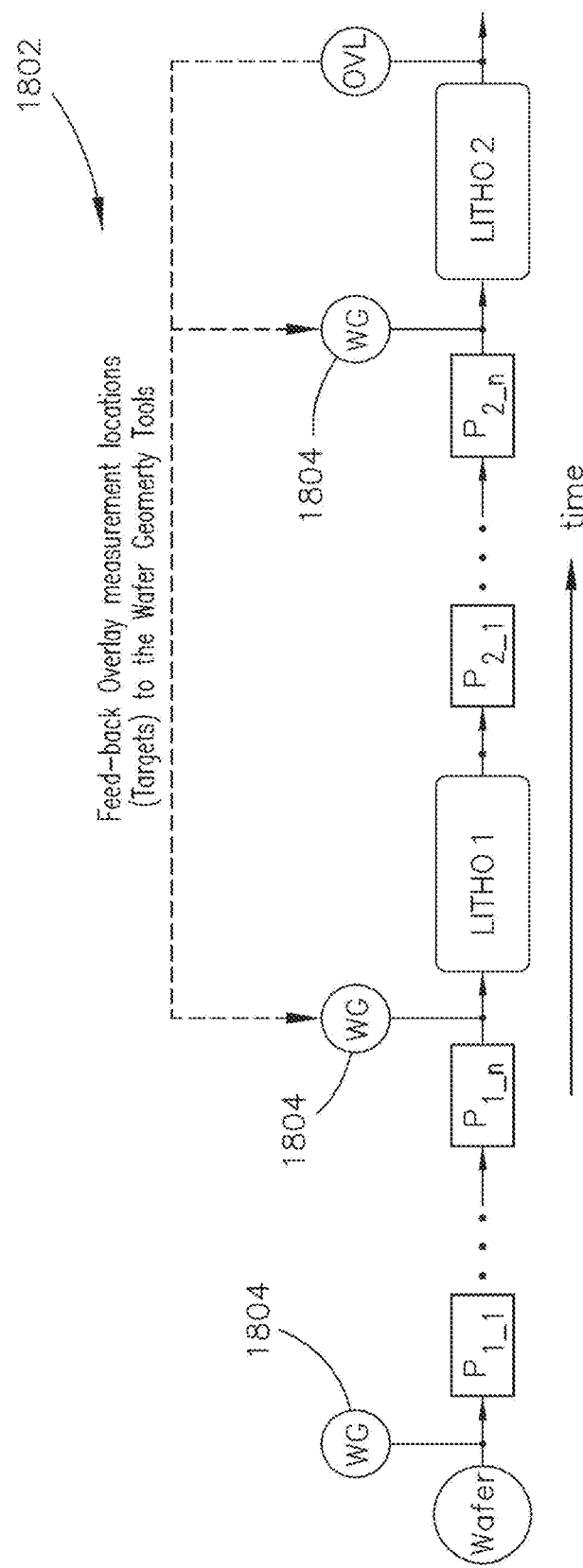
FIG. 18 is an illustration depicting a wafer lithography process relative to a timeline.

FIG. 16 describes a new methodology for performing intra-field data analysis. Step 1602 may receive the wafer shape data as input and step 1604 may compute the shape slope data by pixel level computation or by polynomial fitting computation method as described above. Using the example of lithography overlay variation, overlay errors are typically measured at a number of pre-determined target locations within a lithography field and across multiple fields within a device wafer. This is shown in FIG. 17. These target locations across the wafer 1702 may be fed back to the wafer geometry tool in order to be used as sampling locations for shape-slope metric or shape-slope residual metric measurement. The development and usage of shape-slope residual metric is described in: Overlay and Semiconductor Process Control Using a Wafer Geometry Metric, P. Vukkadala et al., U.S. patent application Ser. No. 13/476,328, which is herein incorporated by reference in its entirety. Furthermore, the feed-back loop 1802 for feeding process measure locations to the wafer geometry tool 1804 is illustrated in FIG. 18, which depicts a wafer lithography process relative to a timeline.

Step 1606 may then obtain the shape slope data and other higher-order shape (HOS) data for certain user specified target locations and step 1608 may utilize the shape slope data at these target locations to study intra-field lithography process variation such as overlay variation. The HOS values measured at these target locations may then be utilized to perform intra-field data analysis in step 1610. For instance, step 1610 may compare the HOS values measured at these target locations to process data such as overlay errors (using visual color maps or statistical correlation analysis) in order to identify the correlation between HOS values and process variation. Such analysis can be used to assess the impact of HOS on intra-field process variation.

It is contemplated that alternative approaches may also be utilized for assessing the impact of HOS on inter-field process variations. For instance, the process data such as overlay data (measured at several targets per field and at multiple fields across the wafer) may be partitioned and re-formatted into sites (fields) and sectors exactly similar to the partitioning scheme used with the corresponding wafer geometry data. Thus metrics such as mean overlay, peak-to-valley overlay and the like may be computed per field/sector for multiple fields/sectors across the wafer. This may then be compared to site-based or sector-based wafer geometry metrics to assess the impact of wafer geometry variation (HOS) on inter-field process variation.

It is also contemplated that the site based high order shape analysis method and system in accordance with the present disclosure may be appreciated in various other wafer analysis applications. For example, the various HOS metrics described above may be utilized to control a Chemical Mechanical Planarization or Polishing (CMP) process.

Figure 19:
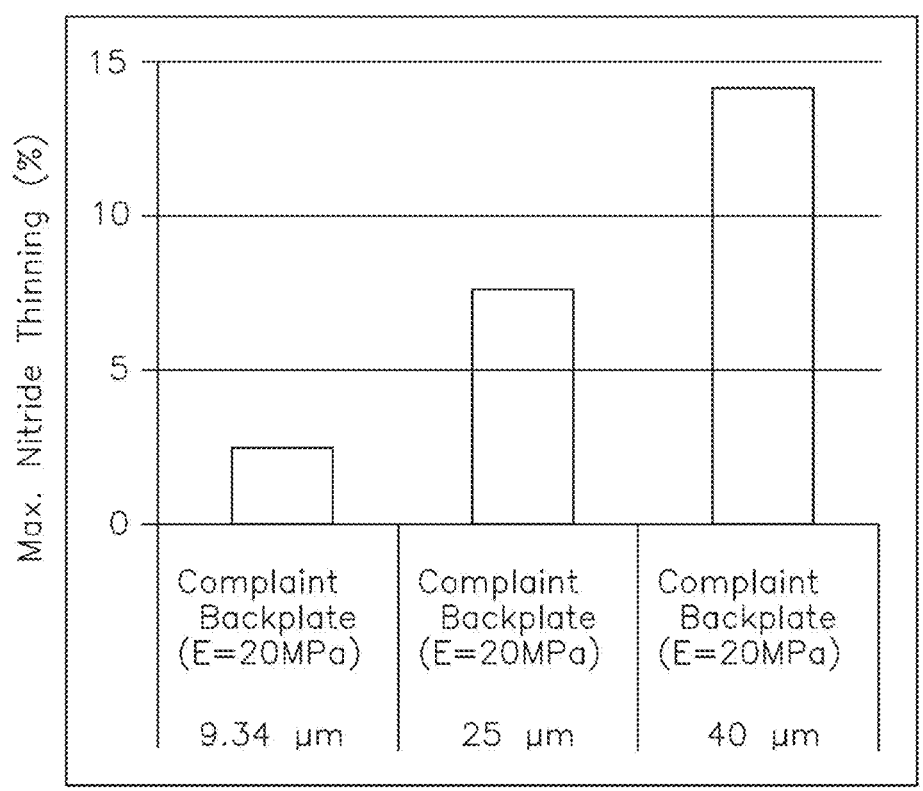
FIG. 19 is an illustration depicting the relationship between the amount of nitride thinning experienced as the magnitude of wafer lip increases.

More specifically, modeling simulation results reported in P. Vukkadala et al., "Impact of Wafer Geometry on CMP for Advanced Nodes," Journal of Electrochemical Society (JES), Vol. 158, No. 10, pp. H1002-H1009, 2011, shows that the uniformity of CMP processes such as Shallow Trench Isolation (STI) are highly dependent on the higher order components of the shape of a wafer. This is illustrated in FIG. 19, which shows increasing the amount of nitride thinning experienced as the magnitude of wafer lip (a higher order shape component) increases. A typical method for measuring nitride thinning during a CMP process is by measuring the STI step height. The process data such as STI step height variation are typically measured at a finite number of points on the surface of the wafer. To assess the correlation between the process data and the wafer geometry metrics, the process data needs to be formatted appropriately. The methodology for formatting the process data is dependent on the format of the wafer geometry metrics. For example, for comparing the sector metrics the process data will be grouped into various sectors and relevant metrics will be computed on the process data.

Consequently experiments were conducted to assess the impact of higher order shape on CMP removal uniformity. It was determined that the Radial Shape-Slope metric (both sites/polar-sector based) correlated well with the STI step height variation process data. Hence the Radial Shape Slope metric of an unpatterned/filmed wafer may be used to control the uniformity of CMP processes such as STI. This may be achieved by having an inline monitor for Radial Shape Slope to assess the amount of CMP non-uniformity an incoming wafer may exhibit down the line after a CMP process.

Figure 20:
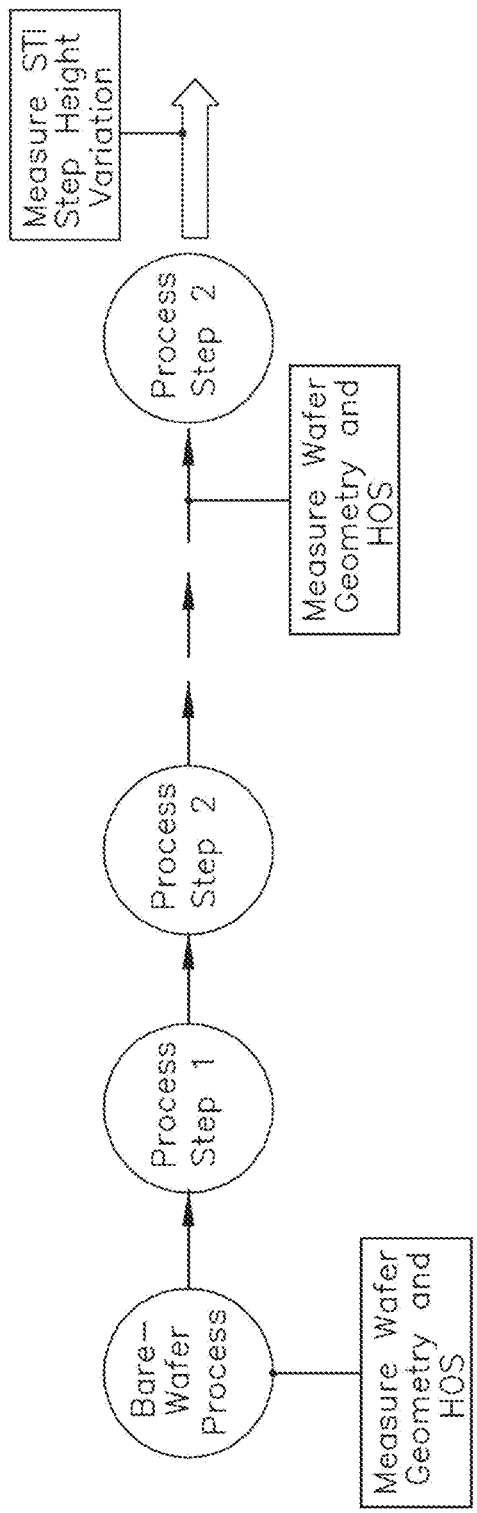
FIG. 20 is a flow diagram illustrating utilizing the site based high order shape analysis to control a Chemical Mechanical Planarization or Polishing (CMP) process.

This is illustrated in FIG. 20 where the wafer geometry (including HOS) is measured at the bare/unpatterned wafer level as well as several process steps later but right before the wafer is subjected to CMP. This way two things may be determined: (i) by computing the difference in higher order shape between the two wafer geometry measurements gives an indication of the amount of higher order shape induced by wafer processing; and (ii) by correlating higher order shape (e.g., Radial Shape Slope) to CMP removal variation across the wafer a model may be developed for predicting the amount of CMP variation that may be caused by a given wafer higher order shape. Proper thresholds for the wafer high order shapes may be developed to limit the amount of CMP variation to an acceptable level. Thus an inline wafer geometry (higher order shape) monitor may be used to: (i) accept/reject a wafer for a particular process, (ii) identify process steps that induce larger higher order shape for further root-cause-analysis, and (iii) sort incoming wafers into technology node specific bins.

Another example of the application of wafer site based higher order shape metrics is to monitor the impact of wafer shape on a lithography process. When patterning a wafer using a lithography process, the wafer is first held on a vacuum or electrostatic chuck (based on the lithography technology) by using vacuum or electrostatic force respectively. When the wafer is held on a chuck using a force, the initial gap between the wafer and chuck primarily due to the shape of the wafer is reduced. Ideally the wafer back surface is expected to completely come in contact with the chuck surface with zero contact gap. However, in reality the contact gap is a function of the wafer geometry. A contact gap may result in defocus errors and needs to be monitored and controlled. Previously, there was no metric to monitor the contact gap during chucking.

Figure 21:
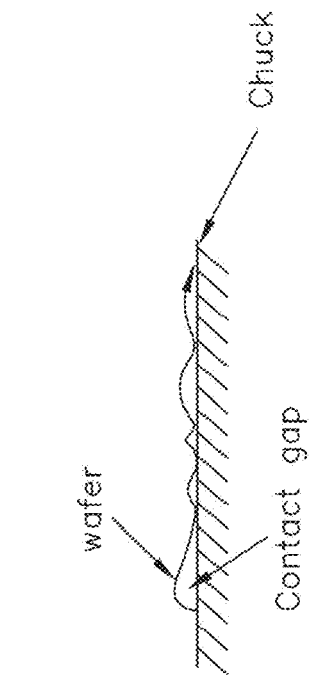
FIG. 21 is an illustration depicting contact gap(s) before and after chucking.
Figure 21:
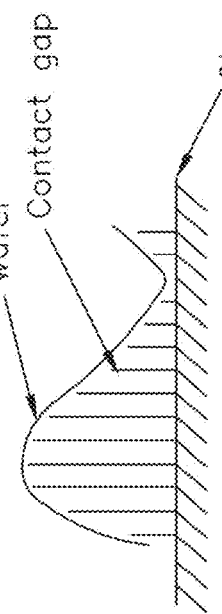
Figure 22:
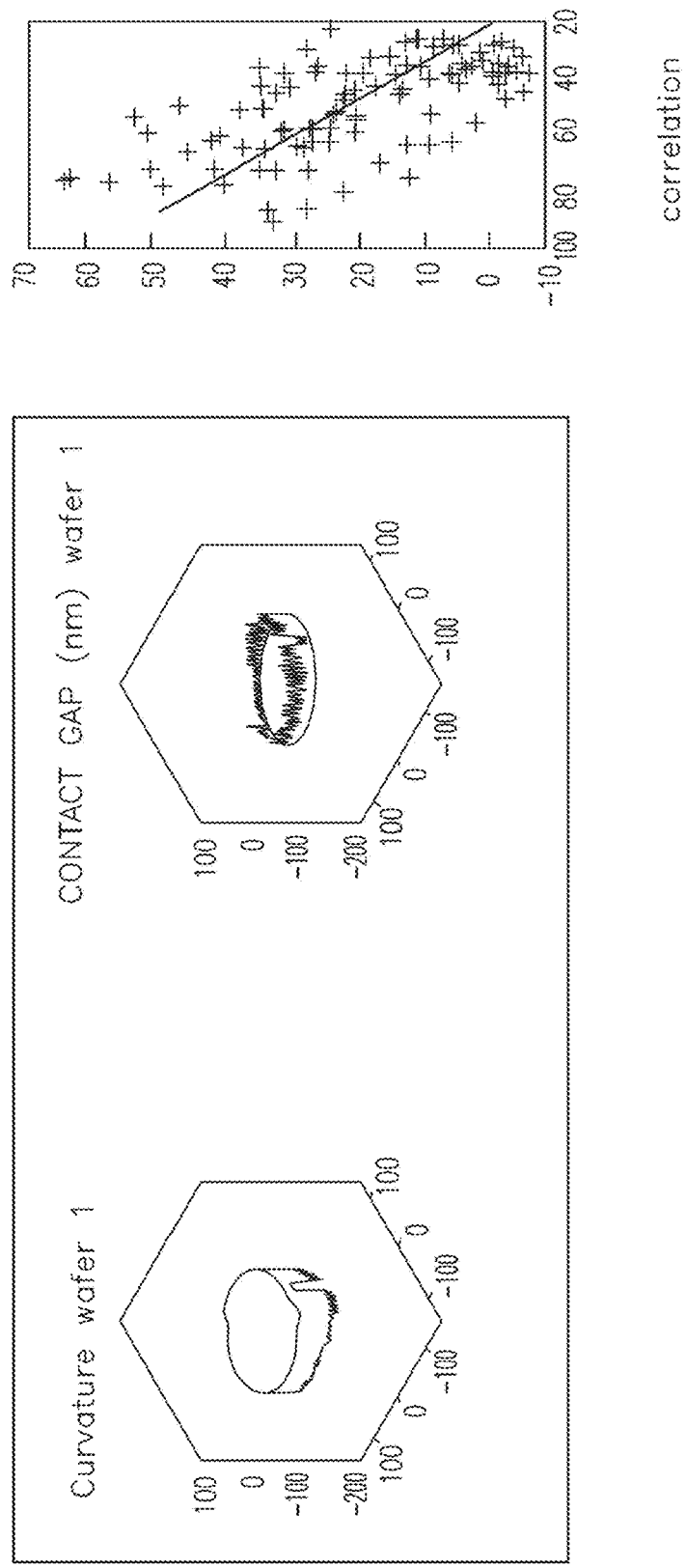
FIG. 22 is an illustration depicting the observed correlation between contact gap and site based shape curvature metrics.

FIG. 21 illustrates the change of the contact gap(s) as a result of chucking. Consequently, a three-dimensional finite element model with tens of thousands of nodes may be developed to simulate the wafer and chuck interaction. The key input parameters of the model may include the wafer geometry, the chuck geometry, and the applied vacuum/electrostatic pressure. This model may be developed assuming uniform chucking pressure over the entire surface of the wafer. One of the key outputs of the model may include contact gap estimation. With the pressure and chuck geometry being constant, the impact on different wafer geometry on contact gap may be estimated/observed. Experimental results have indicated that contact gap is a function of the curvature of wafer shape and a good correlation was observed between contact gap and the site based shape curvature metric as shown in FIG. 22. Therefore, the site based shape curvature metrics provided utilizing the method and system of the present disclosure may be utilized to monitor/access the impact of wafer shape on a lithography process.

Figure 23:
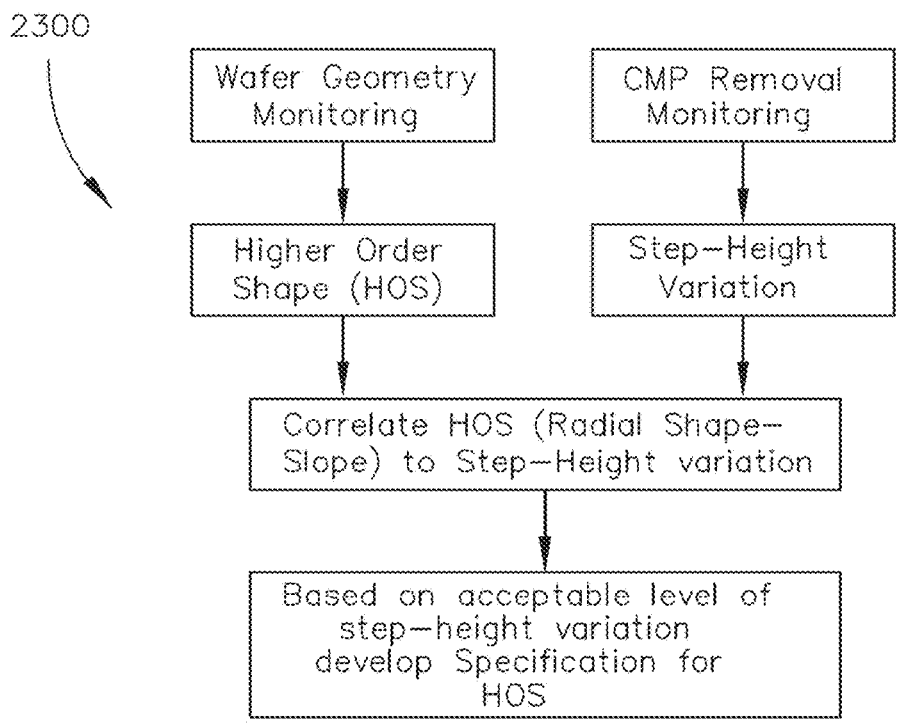
FIG. 23 is a flow diagram illustrating utilizing the site based high order shape analysis for specification development.
Figure 24:
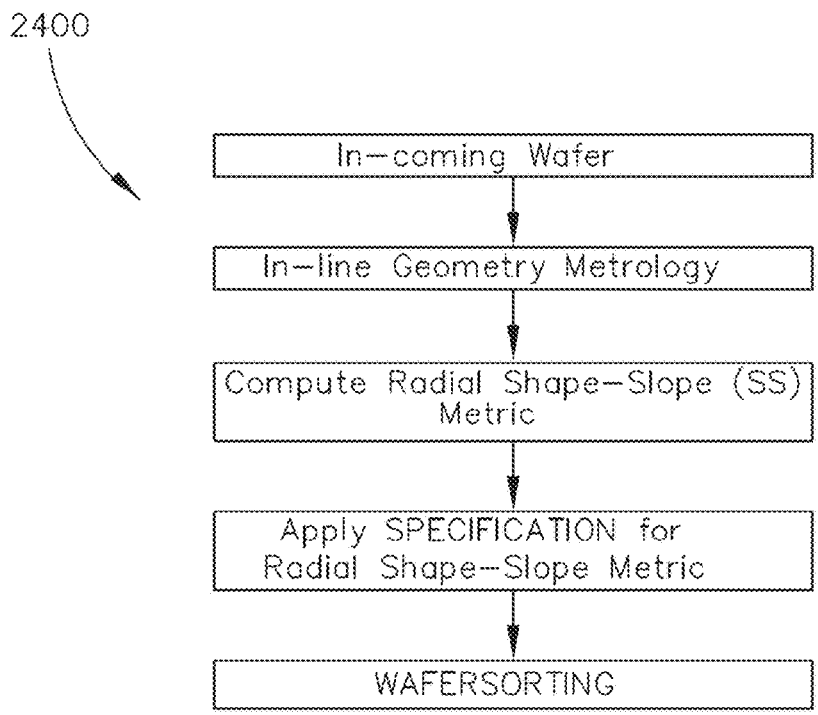
FIG. 24 is a flow diagram illustrating utilizing the site based high order shape analysis for an unpatterned wafer geometry control process.
Figure 25:
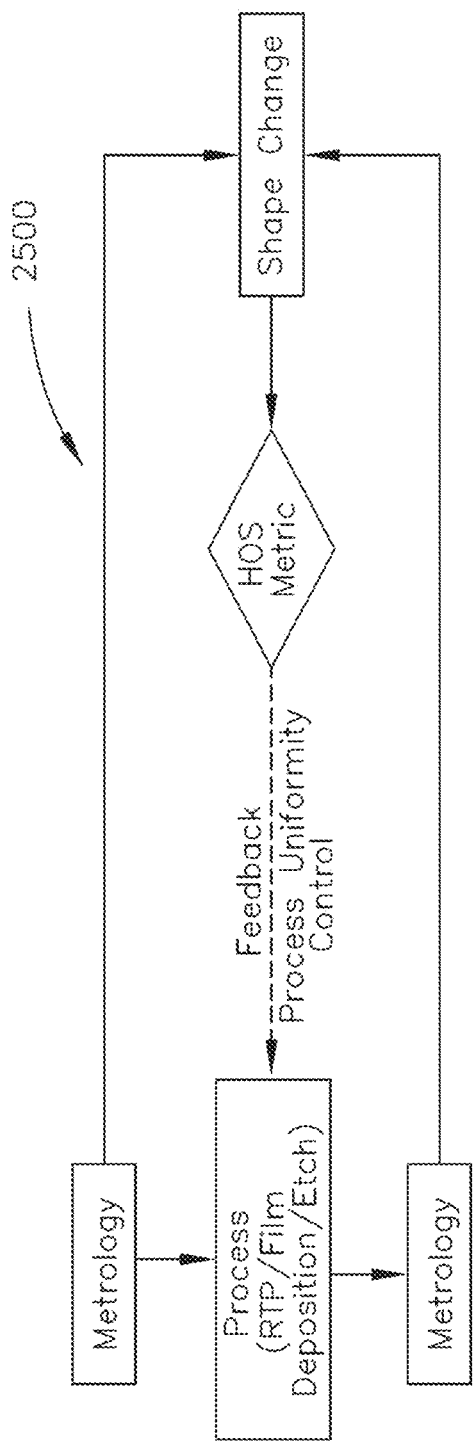
FIG. 25 is a flow diagram illustrating utilizing the site based high order shape analysis for process uniformity control.

In addition to utilizing the HOS metrics to control a CMP and lithography process, it is contemplated that the HOS metrics may be utilized for controlling other processes without departing from the spirit and scope of the present disclosure. For instance, FIG. 23 is a flow diagram depicting utilizing HOS metrics for specification development, FIG. 24 is a flow diagram depicting an unpatterned wafer geometry control process, and FIG. 25 is a flow diagram depicting process uniformity control, all based on the HOS metrics described in accordance with the present disclosure. It is also contemplated that the HOS metrics may be utilized for process control for mitigating overlay errors as well as other wafer analysis/control applications.

Figure 26:
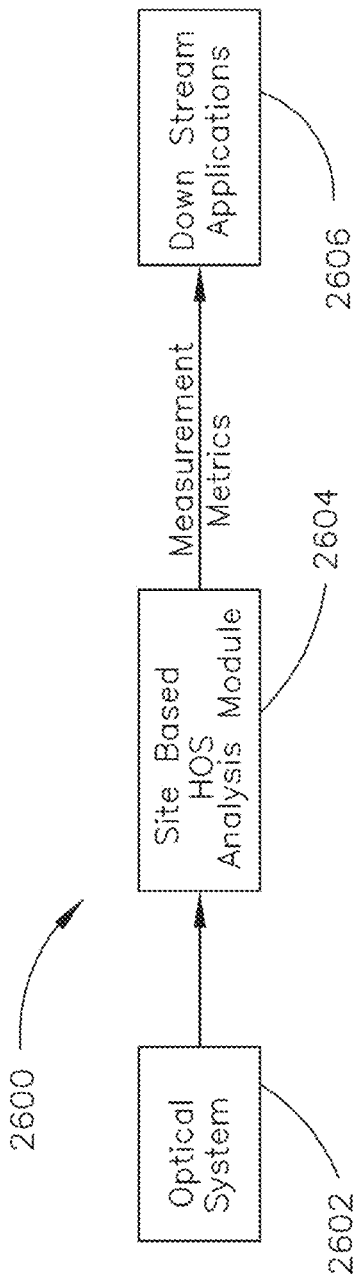
FIG. 26 is a block diagram illustrating a system for inspecting a wafer in accordance with the present disclosure.

FIG. 26 is a block diagram depicting a wafer inspection system 2600 in accordance with the present disclosure. The wafer inspection system 2600 includes an optical system 2602 configured for obtaining a wafer surface image. As previously described, the optical system 2602 may acquire the wafer surface images directly utilizing wafer dimensional geometry tools such as the WaferSight metrology system from KLA-Tencor. Alternatively, the wafer shape image, wafer front and back surface shape images or the like may also be constructed indirectly using other metrology tools as well.

The wafer inspection system 2600 also includes a site based high order wafer shape analysis module 2604 in communication with the optical system 2602. The site based high order wafer shape analysis module 2604 is configured for carrying out the site based high order shape analysis method 100 as described above. The calculated high order shape metrics may subsequently be utilized as control input for various downstream applications 2606, including, but not limited to, CMP processes, wafer specification development processes, unpatterned wafer geometry control processes, wafer uniformity control processes or the like.

Figure 27:
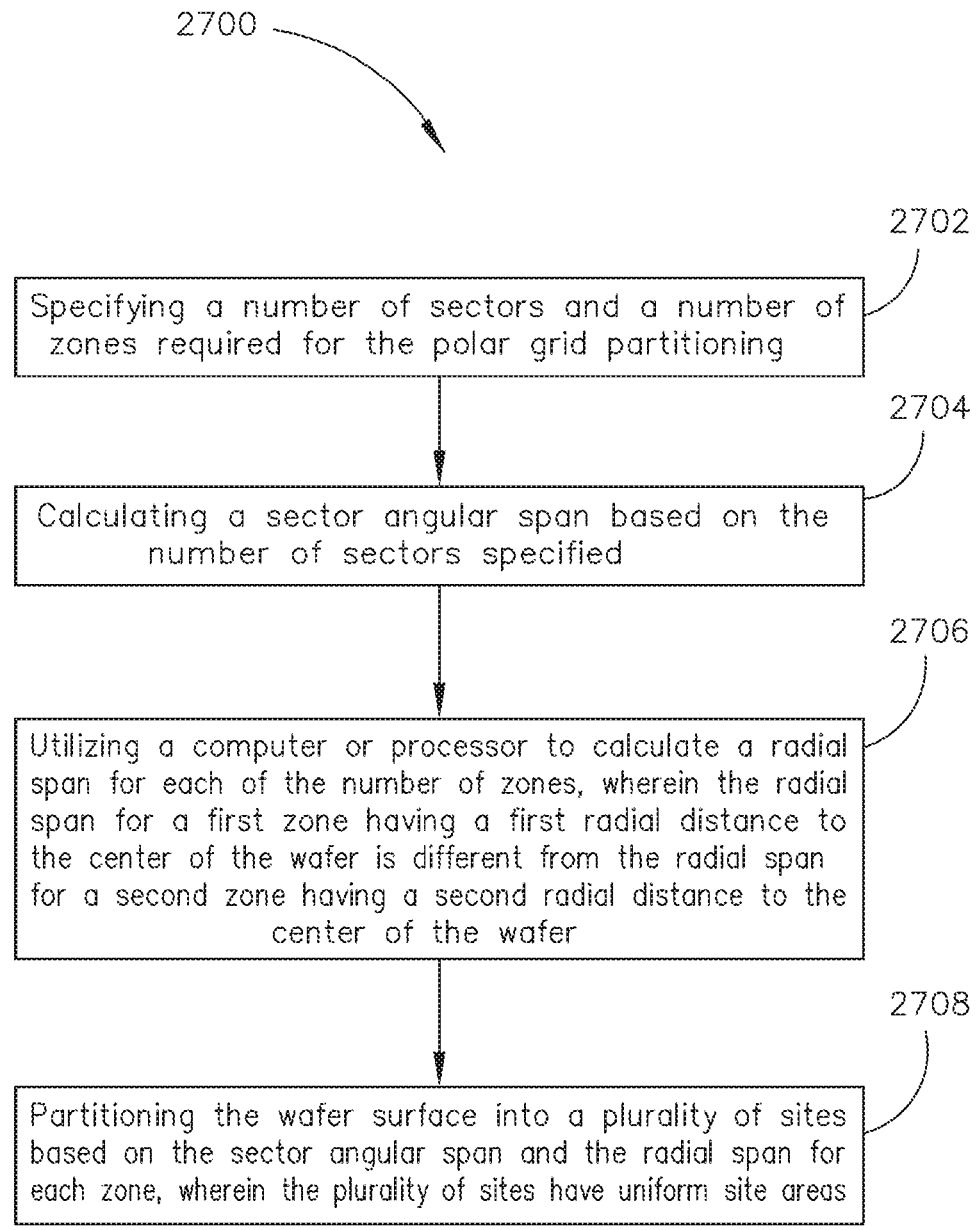
FIG. 27 is a flow diagram illustrating a polar grid partitioning method in accordance with the present disclosure.

FIG. 27 is a flow diagram illustrating the polar grid partitioning method 2700 in accordance with the present disclosure. Step 2702 may specify a number of sectors and a number of zones required for the polar grid partitioning. Step 2704 may calculate a sector angular span based on the number of sectors specified. Step 2706 may calculate a radial span for each of the number of zones. In accordance with this partitioning scheme, the radial span for a first zone having a first radial distance to the center of the wafer is different from the radial span for a second zone having a second radial distance to the center of the wafer. Step 2708 may then partition the wafer surface into a plurality of sites based on the sector angular span and the radial span for each zone. The sites partitioned in this manner will have uniform site areas.

Figure 28:
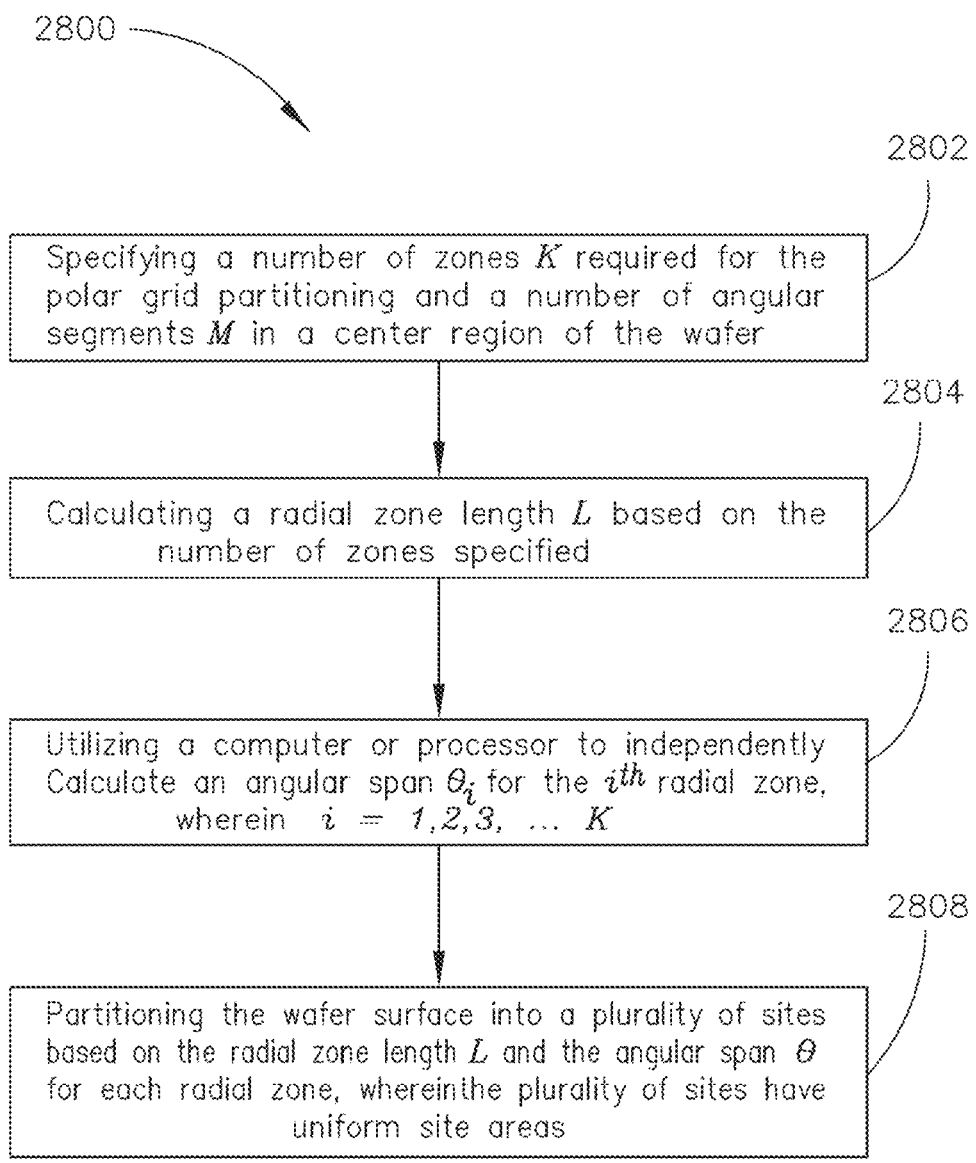
FIG. 28 is a flow diagram illustrating another polar grid partitioning method in accordance with the present disclosure.

FIG. 28 is a flow diagram illustrating an alternative polar grid partitioning method 2800 in accordance with the present disclosure. Step 2802 may specify a number of zones K required for the polar grid partitioning and a number of angular segments M in a center region of the wafer. Step 2804 may calculate a radial zone length L based on the number of zones specified. Step 2806 may independently calculate an angular span $\theta_i$ for the $i^{th}$ radial zone, wherein i=1, 2, 3, . . . K. Step 2808 may subsequently partition the wafer surface into a plurality of uniform sites based on the radial zone length L and the angular span $\theta$ for each radial zone. The sites partitioned in this manner will have uniform site areas.

It is contemplated that while the examples above referred to wafer metrology measurements, the systems and methods in accordance with the present disclosure are applicable to other types of polished plates as well without departing from the spirit and scope of the present disclosure. The term wafer used in the present disclosure may include a thin slice of semiconductor material used in the fabrication of integrated circuits and other devices, as well as other thin polished plates such as magnetic disc substrates, gauge blocks and the like.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A polar grid partitioning method for partitioning a wafer surface, the method comprising:
   specifying a number of sectors and a number of zones required for the polar grid partitioning;
   calculating, with one or more processors, a sector angular span based on the number of sectors specified;
   calculating, with one or more processors, a radial span for each of the number of zones, wherein the radial span for a first zone having a first radial distance to the center of the wafer is different from the radial span for a second zone having a second radial distance to the center of the wafer;
   partitioning, with one or more processors, the wafer surface into a plurality of sites based on the sector angular span and the radial span for each zone to improve accuracy of wafer shape analysis performed on the wafer, wherein the plurality of sites have uniform site areas;
   calculating, with one or more processors, one or more measurement metrics based on the partitioning of the wafer surface into the plurality of sites based on the sector angular span and the radial span for each zone; and
   providing, with one or more processors, the one or more measurement metrics to control a process of one or more process tools.

2. The polar grid partitioning method of claim 1, wherein the radial span for the first zone is greater than the radial span for the second zone when the first radial distance is smaller than the second radial distance.

3. The polar grid partitioning method of claim 1, wherein the radial span for the $i^{th}$ radial zone is defined as the span between boundaries:

$r_i = \sqrt{i}L$ and $r_{i-1} = \sqrt{i-1}L$, i=1,2,3, . . . K wherein $$L = \frac{R}{\sqrt{K}},$$

and R is the radius of the wafer and K is the number of zones.

4. The method of claim 1, wherein the one or more measurement metrics includes at least one of:
   a plurality of surface shape metrics; and
   a plurality of deviation metrics.

5. The method of claim 1, wherein the one or more measurement metrics are calculated based on surface coefficients obtained utilizing at least one of: a polynomial fitting process or a pixel-based shape-slope computation process.

6. The method of claim 1, wherein the one or more measurement metrics are utilized for controlling at least one of: a Chemical Mechanical Planarization or Polishing (CMP) process, a wafer specification development process, an unpatterned wafer geometry control process, or a wafer uniformity control process.

7. The method of claim 4, wherein the surface shape metrics includes at least one of:
- an average slope of a measurement site in x-direction;
- an average slope of a measurement site in y-direction;
- a magnitude of a measurement site slope;
- a magnitude of a second order surface component for a measurement site;
- a radial slope of a measurement site; or
- a tangential slope of a measurement site.

8. A polar grid partitioning method for partitioning a wafer surface, the method comprising:
- specifying a number of zones K required for the polar grid partitioning and a number of angular segments M in a center region of the wafer;
- calculating, with one or more processors, a radial zone length L based on the number of zones specified;
- calculating, with one or more processors, an angular span $\theta_i$ for the $i^{th}$ radial zone, wherein i=1, 2, 3, . . . K;
- partitioning, with one or more processors, the wafer surface into a plurality of sites based on the radial zone length L and the angular span for each radial zone to improve accuracy of wafer shape analysis performed on the wafer, wherein the plurality of sites have uniform site areas;
- calculating, with one or more processors, one or more measurement metrics based on the partitioning of the wafer surface into the plurality of sites based on the radial zone length L and the angular span for each radial zone; and
- providing, with one or more processors, the one or more measurement metrics to control a process of one or more process tools.

9. The polar grid partitioning method of claim 8, wherein the angular span $\theta_i$ is less than the angular span $\theta_{i-1}$ for i>1.

10. The polar grid partitioning method of claim 9, wherein the angular span $\theta_i$ for the $i^{th}$ radial zone is calculated according to equation:

$$\theta_i = \frac{1}{2i-1}\frac{2\pi}{M}, i = 1, 2, 3, \ldots K.$$

11. The method of claim 8, wherein the one or more measurement metrics includes at least one of:
- a plurality of surface shape metrics; and
- a plurality of deviation metrics.

12. The method of claim 8, wherein the one or more measurement metrics are calculated based on surface coefficients obtained utilizing at least one of: a polynomial fitting process or a pixel-based shape-slope computation process.

13. The method of claim 8, wherein the one or more measurement metrics are utilized for controlling at least one of: a Chemical Mechanical Planarization or Polishing (CMP) process, a wafer specification development process, an unpatterned wafer geometry control process, or a wafer uniformity control process.

14. The method of claim 11, wherein the surface shape metrics includes at least one of:
- an average slope of a measurement site in x-direction;
- an average slope of a measurement site in y-direction;
- a magnitude of a measurement site slope;
- a magnitude of a second order surface component for a measurement site;
- a radial slope of a measurement site; or
- a tangential slope of a measurement site.

* * * * *